US008377929B2

(12) United States Patent
Nudelman et al.

(10) Patent No.: US 8,377,929 B2
(45) Date of Patent: Feb. 19, 2013

(54) CRYSTALLINE FORMS OF THE TRI-MESYLATE SALT OF PERPHENAZINE-GABA AND PROCESS OF PRODUCING THE SAME

(75) Inventors: Abraham Nudelman, Rechovot (IL); Ada Rephaeli, Herzlia (IL); Irit Gil-Ad, Herzlia (IL); Abraham Weizman, Tel-Aviv (IL); Mazal Shaul, Azur (IL); Efrat Halbfinger, RaAnana (IL)

(73) Assignees: Ramot at Tel-Aviv University Ltd., Tel-Aviv (IL); Bar-Ilan University, Ramat-Gan (IL); BioLineRX Ltd., Jerusalem (IL)

( * ) Notice: Subject to any disclaimer, the term of this patent is extended or adjusted under 35 U.S.C. 154(b) by 0 days.

(21) Appl. No.: 13/034,453

(22) Filed: Feb. 24, 2011

(65) Prior Publication Data

US 2011/0312948 A1    Dec. 22, 2011

Related U.S. Application Data

(60) Provisional application No. 61/307,481, filed on Feb. 24, 2010, provisional application No. 61/307,482, filed on Feb. 24, 2010.

(51) Int. Cl.

| *A61K 31/5415* | (2006.01) |
| *C07D 417/06* | (2006.01) |
| *A61P 25/28* | (2006.01) |
| *A61P 25/00* | (2006.01) |
| *A61P 25/18* | (2006.01) |
| *B32B 5/16* | (2006.01) |
| *B65D 79/00* | (2006.01) |

(52) U.S. Cl. ........... 514/225.8; 544/45; 544/36; 544/44; 428/402; 206/459.5; 514/659; 514/226.2

(58) Field of Classification Search ........................ None
See application file for complete search history.

(56) References Cited

U.S. PATENT DOCUMENTS

| 3,966,930 | A |   | 6/1976 | Buus et al. |
| 5,145,684 | A | * | 9/1992 | Liversidge et al. ........... 424/489 |
| 5,525,727 | A |   | 6/1996 | Bodor |
| 6,294,562 | B1 |   | 9/2001 | Stilz et al. |
| 2004/0092504 | A1 |   | 5/2004 | Benja-Athon |
| 2006/0046967 | A1 |   | 3/2006 | Satyam |
| 2007/0219181 | A1 |   | 9/2007 | Kimura et al. |
| 2009/0215809 | A1 |   | 8/2009 | Yao et al. |

FOREIGN PATENT DOCUMENTS

| CA | 2461663 | 4/2003 |
| GB | 2188630 | 10/1987 |
| JP | 62-240660 | 10/1987 |
| JP | 10-059948 | 3/1998 |
| JP | 11-506723 | 6/1999 |
| JP | 2001-501965 | 2/2001 |
| JP | 2001-519754 | 10/2001 |
| JP | 2005-503423 | 2/2005 |
| JP | 2005-097120 | 4/2005 |
| WO | WO 96/40687 | 12/1996 |
| WO | WO 97/02819 | 1/1997 |
| WO | WO 98/17678 | 4/1998 |
| WO | WO 98/52898 | 11/1998 |
| WO | WO 01/39779 | 6/2001 |
| WO | WO 03/055424 | 7/2003 |
| WO | WO2006/131923 | * 12/2006 |
| WO | WO 2011/104637 | 9/2011 |
| WO | WO 2012/038963 | 3/2012 |

OTHER PUBLICATIONS

Morissette et al. In Advanced Drug Delivery Reviews 56 (2004) 275-300.*
Response Dated Nov. 24, 2011 to Official Action of Aug. 25, 2011 From the US Patent and Trademark Office Re. U.S. Appl. No. 12/655,048.
Supplemental After Final Amendment Dated Nov. 17, 2011 in Response to Official Action Dated Aug. 5, 2011 From the US Patent and Trademark Office Re. U.S. Appl. No. 12/764,124.
Translation of Office Action Dated Nov. 3, 2011 From the State Intellectual Property Office of the People's Republic of China Re.: Application No. 200580017025.1.
International Search Report and the Written Opinion Dated Dec. 1, 2011 From the International Searching Authority Re. Application No. PCT/IB2011/000915.
Notice of Allowance Dated Dec. 1, 2011 From the US Patent and Trademark Office U.S. Appl. No. 12/764,124.
Official Action Dated Nov. 22, 2011 From the US Patent and Trademark Office Re. U.S. Appl. No. 12/309,361.
Benja-Athon.
Official Action Dated Mar. 14, 2011 From the US Patent and Trademark Office Re. U.S. Appl. No. 12/764,124.
Response Dated Jul. 6, 2011 to Official Action of Mar. 14, 2011 From the US Patent and Trademark Office Re. U.S. Appl. No. 12/764,124.
Examination Report Dated Jun. 8, 2011 From the Instituto Mexicano de la Propriedad Industrial Re. Application No. MX/a/2007/015511 and Its Summary Into English.
Response Dated Feb. 25, 2011 to Official Action of Aug. 25, 2010 From the US Patent and Trademark Office Re. U.S. Appl. No. 12/764,124.
Office Action Dated Mar. 2, 2011 From the Israeli Patent Office Re. Application No. 196538.
Response Dated Aug. 2, 2011 to Office Action of Mar. 2, 2011 From the Israeli Patent Office Re. Application No. 196538.

(Continued)

*Primary Examiner* — Dennis Heyer

(57) ABSTRACT

Novel crystalline form of perphenazine 4-aminobutyrate trimesylate and a process of producing the same are disclosed. The novel crystalline form is characterized by a unique XRPD pattern and a DSC that exhibits an endothermic peak at a relatively high temperature (e.g., higher than 209° C.). Also disclosed are a process of preparing perphenazine 4-aminobutyrate trimesylate by in situ deprotection and salification, in a single-step synthesis, and a highly pure perphenazine 4-aminobutyrate trimesylate obtained thereby. Uses of any of the described perphenazine 4-aminobutyrate trimesylate are also disclosed.

25 Claims, 9 Drawing Sheets

OTHER PUBLICATIONS

Response Dated Jul. 24, 2011 to Communication Pursuant to Article 94(3) EPC of Apr. 11, 2011 From the European Patent Office Re. Application No. 09711260.1.
Response Dated Jul. 26, 2011 to Official Action of Mar. 14, 2011 From the US Patent and Trademark Office Re. U.S. Appl. No. 12/764,124.
Response Dated Jul. 26 to Communication Pursuant to Rules 70(2) and 70a(2) EPC of Jan. 31, 2011 From the European Patent Office Re. Application No. 10182948.9.
English Summary of Examination Report Dated Sep. 4, 2007 From the Instituto Mexicano de la Propriedad Industrial Re. Application No. PA/a/2004/002912.
Examination Report Dated Sep. 20, 2010 From the Instituto Mexicano der la Propriedad Industrial Re. Application No. MX/a/2007/015511 and Its Translation Into English.
Office Action Dated Jun. 24, 2011 From the State Intellectual Property Office of the People's Republic of China Re. Application No. 200780033294.6 and Its Translation Into English.
Response Dated May 5, 2011 to Requisition by the Examiner of Nov. 8, 2010 From the Canadian Intellectual Property Office Re. Application No. 2,461,663.
Response Dated Jun. 6, 2011 to Official Action of Jan. 6, 2011 From the US Patent and Trademark Office Re. U.S. Appl. No. 12/656,048.
Response Dated Feb. 18, 2011 to Examination Report Dated Sep. 20, 2010 From the Instituto Mexicano der la Propriedad Industrial Re. Application No. MX/a/2007/015511 and Its Translation Into English.
Interview Summary Dated Jan. 27, 2011 From the US Patent and Trademark Office Re.: U.S. Appl. No. 12/585,021.
Notice of Allowance Dated Mar. 21, 2011 From the US Patent and Trademark Office Re.: U.S. Appl. No. 12/585,021.
Official Action Dated Jul. 12, 2011 From the US Patent and Trademark Office Re. U.S. Appl. No. 11/921,578.
Response Dated Mar. 9, 2011 to Official Action of Dec. 14, 2010 From the US Patent and Trademark Office Re.: U.S. Appl. No. 12/585,021.
Response Dated Jun. 16, 2011 to Communication Pursuant to Article 94(3) EPC of Dec. 16, 2010 From the European Patent Office Re. Application No. 02772790.8.
Response Dated Sep. 18, 2011 to Examination Report of Jun. 16, 2011 From the Instituto Mexicano de la Propriedad Industrial Re. Application No. PA/a/2006/010924.
Communication Under Rule 71(3) EPC Dated Sep. 21, 2011 From the European Patent Office Re. Application No. 02772790.8.
Response Dated Oct. 3, 2011 to Office Action of Jun. 6, 2010 From the Israeli Patent Office Re.: Application No. 161083.
Official Action Dated Nov. 1, 2011 From the US Patent and Trademark Office Re. U.S. Appl. No. 11/921,578.
Bastin et al. "Salt Selection and Optimisation Procedures for Pharmaceutical New Chemical Entities", Organic Process Research & Development, 4: 427-435, 2000.
Official Action Dated Aug. 5, 2011 From the US Patent and Trademark Office Re. U.S. Appl. No. 12/764,124.
Response Dated Aug. 22, 2011 to Office Action of Jun. 24, 2011 From the State Intellectual Property Office of the People's Republic of China Re. Application No. 200780033294.6.
Official Action Dated Aug. 25, 2011 From the US Patent and Trademark Office Re. U.S. Appl. No. 12/655,048.
Requisition by the Examiner Dated Aug. 2, 2011 From the Canadian Intellectual Property Office Re. Application No. 2,560,905.
Response Dated Oct. 3, 2011 to Examination Report of Jun. 8, 2011 From the Instituto Mexicano de la Propriedad Industrial Re. Application No. MX/a/2007/015511.
Advisory Action Before the Filing of an Appeal Brief Dated Oct. 25, 2011 From the US Patent and Trademark Office Re. U.S. Appl. No. 12/764,124.
Examiner's Report Dated Oct. 7, 2011 From the Australian Government, IP Australia Re. Application No. 2007274583.
Translation of Notice of Reason for Rejection Dated Sep. 30, 2011 From the Japanese Patent Office Re. Application No. 2007-504560.
Official Action Dated Oct. 21, 2011 From the US Patent and Trademark Office Re. U.S. Appl. No. 12/373,542.

Response Dated Oct. 19, 2011 to Official Action Dated Aug. 5, 2011 From the US Patent and Trademark Office Re. U.S. Appl. No. 12/764,124.
Response Dated Oct. 23, 2011 to Office Action Dated May 17, 2011 From the Israel Patent Office Re.: Application No. 187892.
Bousquet et al. "Synthesis, Physical Properties, Toxicological Studies and Bioavailability of L-Pyroglutamic and L-Glutamic Acid Esters of Paracetamol as Potentially Prodrugs", Journal of Pharmacy and Pharmacology, 48: 479-485, Jan. 1996.
Response Dated Jul. 20, 2011 to Notice of Final Rejection of May 30, 2011 From the Korean Intellectual Property Office Re. Application No. 2010-7016372.
Office Action Dated Dec. 12, 2011 From the Israel Patent Office Re.: Application No. 187892 and Its Translation Into English.
Requisition by the Examiner Dated Aug. 2, 2011 From the Canadian Intellectual Property Office Re. Application No. 2,461,663.
Response Dated Sep. 7, 2011 to Official Action of Jul. 12, 2011 From the US Patent and Trademark Office Re. U.S. Appl. No. 11/921,578.
Translation of Final Notice of the Reason for Rejection Dated Aug. 31, 2011 From the Korean Intellectual Property Office Re. Application No. 2010-7016372.
Response Dated Dec. 14, 2011 to Notice of Reason for Rejection of Sep. 30, 2011 From the Japanese Patent Office Re. Application No. 2007-504560.
Response Dated Dec. 15, 2011 to Examiner's Report of Oct. 21, 2010 From the Australian Government, IP Australia Re. Application No. 2006256369.
Response Dated Aug. 23, 2011 to Official Action of Jun. 23, 2011 From the US Patent and Trademark Office Re. U.S. Appl. No. 12/373,542.
Communication Under Rule 71(3) EPC Dated Nov. 28, 2011 From the European Patent Office Re. Application No. 07789958.1.
Translation of Notice of Reason for Rejection Dated Nov. 29, 2011 From the Japanese Patent Office Re. Application No. 2008-515378.
Communication Under Rule 71(3) EPC Dated Feb. 20, 2012 From the European Patent Office Re. Application No. 09711260.1.
Notice of Allowance Dated Feb. 23, 2012 From the US Patent and Trademark Office Re. U.S. Appl. No. 12/867,055.
Translation of Office Action Dated Feb. 23, 2012 From the State Intellectual Property Office of the People's Republic of China Re. Application No. 200780033294.6.
Official Action Dated Jan. 31, 2012 From the US Patent and Trademark Office Re. U.S. Appl. No. 12/309,361.
Applicant-Initiated Interview Summary Dated Apr. 19, 2012 From the US Patent and Trademark Office Re. U.S. Appl. No. 12/655,048.
Notice of Allowance Dated Apr. 12, 2012 From the US Patent and Trademark Office Re. U.S. Appl. No. 12/373,542.
Translation of Office Action Dated Jan. 30, 2012 From the State Intellectual Property Office of the People's Republic of China Re.: Application No. 200680029378.8.
Translation of Office Action Dated Jan. 5, 2012 From the State Intellectual Property Office of the People's Republic of China Re. Application No. 200810190781.X.
Advisory Action Before the Filing of an Appeal Brief Dated Jan. 10, 2012 From the US Patent and Trademark Office Re. U.S. Appl. No. 12/655,048.
Examination Report Dated Dec. 5, 2011 From the Instituto Mexicano de la Propriedad Industrial Re. Application No. MX/a/2009/000641 and Its Summary in English.
Examiner's Report Dated Jan. 24, 2012 From the Australian Government, IP Australia Re. Application No. 2006256369.
Communication Pursuant to Article 94(3) EPC Dated Jan. 26, 2012 From the European Patent Office Re. Application No. 10182948.9.
Examination Report Dated Jan. 19, 2012 From the Instituto Mexicano de la Propriedad Industrial Re. Application No. MX/a/2007/015511 and Its Translation Into English.
International Search Report and the Written Opinion Dated Feb. 8, 2012 From the International Searching Authority Re.: Application No. PCT/IL2011/000752.
Official Action Dated Feb. 2, 2012 From the US Patent and Trademark Office Re. U.S. Appl. No. 12/655,048.

Summons to Attend Oral Proceedings Pursuant to Rule 115(1) EPC Dated Jan. 26, 2012 From the European Patent Office Re. Application No. 06756205.8.

Rephaeli et al. "Gamm-Aminobutyric Acid Amides of Nortriptyline and Fluoxetine Display Improved Pain Suppressing Activity", Journal of Medicinal Chemistry, XP002668033, 52(9): 3010-3017, 2009. Scheme 1, Experimental Section.

Advisory Action Before the Filing of an Appeal Brief Dated Jan. 10, 2012 From the US Patent and Trademark Office Re. U.S. Appl. No. 12/656,048.

Applicant-initiated interview Summary Dated Apr. 19, 2012 From the US Patent and Trademark Office Re. U.S. Appl. No. 12/656,048.

Examiner's Report Dated Jan. 19, 2012 From the Australian Government, IP Australia Re. Application No. 2006256369.

Official Action Dated Feb. 2, 2012 From the US Patent and Trademark Office Re. U.S. Appl. No. 12/656,048.

Official Action Dated Aug. 25, 2011 From the US Patent and Trademark Office Re. U.S. Appl. No. 12/656,048.

Official Action Dated May 2003 From the US Patent and Trademark Office Re. U.S. Appl. No. 11/921,578.

Bryson et al. "Amitriptyline. A Review of Its Pharmacological Properties and Therapeutic Use in Chronic Pain States", Drug & Aging, 8(6): 459-476, 1996.

* cited by examiner

Lot 01 BIL02-04-22, 280741-2a, 40x objective

Lot 01 BIL02-05-26, File 280748-2a, 40x objective

US 8,377,929 B2

CRYSTALLINE FORMS OF THE TRI-MESYLATE SALT OF PERPHENAZINE-GABA AND PROCESS OF PRODUCING THE SAME

CROSS REFERENCE TO RELATED APPLICATIONS

This application claims priority to U.S. Provisional Application Ser. Nos. 61/307,481 and 61/307,482, both of which were filed Feb. 24, 2010, each of which is incorporated herein by reference in its entirety.

FIELD AND BACKGROUND OF THE INVENTION

The present invention, relates to novel crystalline forms of pharmaceutically active agents and, more particularly, but not exclusively, to novel crystalline forms of chemical conjugates comprised of a psychotropic drug and an organic acid, to processes of producing the same and to uses thereof in the treatment of CNS diseases and disorders.

A series of conjugates of psychotropic drugs and organic acids and their use in the treatment of psychotropic and/or proliferative diseases and disorders are described in detail in International Patent Applications published as WO 03/026563 and WO 2005/092392 and in U.S. Pat. No. 7,544,681, which are all incorporated by reference as if fully set forth herein. These conjugates may exert greater therapeutic efficacy and/or cause fewer and/or less severe side effects than their respective non-conjugated psychotropic drugs. Among the disclosed conjugates is a conjugate that comprises perphenazine covalently linked to γ-aminobutyric acid (GABA).

Acid addition salts of such conjugates in which the organic acid has a free amino group (such as GABA and other GABA agonists) have been disclosed in WO 2006/131923. Among the disclosed salts is a mesylate addition salt of the perphenazine-GABA conjugate prepared by reacting a solution of an N-protected perphenazine-GABA conjugate with methanesulfonic acid to afford, upon filtration, the mesylate salt, having a purity of about 98% according to HPLC measurements.

Crystalline forms, that include polymorphs and pseudopolymorphs, are distinct solids sharing the same structural formula, yet having different physical properties due to different conformations and/or orientations of the molecule in the unit cell of the crystal. The physical characteristics, such as solubility and stability, of different crystalline forms are often different and are thus exceptionally relevant in the field of pharmacology.

For a general review of crystalline forms (i.e. polymorphs and pseudopolymorphs) and the pharmaceutical applications of crystalline forms see Wall *Pharm. Manuf.* 1986, 3, 33; Haleblian et al. *J. Pharm. Sci.* 1969, 58, 911; and Haleblian *J. Pharm. Sci.*, 1975, 64, 1269.

Different crystalline forms of a pharmaceutically useful compound provide opportunities to improve the performance characteristics of a pharmaceutical product. Different crystalline forms enlarge the repertoire of materials that a formulation scientist has available for designing, for example, a pharmaceutical dosage form of a drug with a desired release profile, solubility characteristics or other desired characteristic. It is well known that new crystalline forms of known useful compounds are of utility.

SUMMARY OF THE INVENTION

The present inventors have now discovered that, depending on the reaction conditions used for preparing a trimesylate salt of a perphenazine-GABA conjugate (4-amino-butyric acid 2-{4-[3-2-chloro-phenothiazine-10-yl)propyl]-piperazine-1-yl}-ethyl ester), various crystalline forms of the salt are obtained. The present inventors have therefore designed a process of preparing a crystalline form of a trimesylate salt of a perphenazine-GABA conjugate, which exhibits superior physicochemical performance (e.g., higher stability, reduced hygroscopy), compared to trimesylate salts prepared under other conditions. The present inventors have further characterized the highly stable crystalline form uncovered.

Thus, according to an aspect of some embodiments of the present invention, there is provided a crystalline form of perphenazine 4-aminobutyrate trimesylate (crystalline Form B), characterized by at least one of:

(a) an X-Ray Powder Diffraction (XRPD) pattern exhibiting at least five of the peaks shown in one or more of FIG. 2; and (b) a Differential Scanning calorimetry (DSC) scan exhibiting an endothermic peak at or higher than about 209° C.

According to some embodiments of the invention, the endothermic peak is at about 214° C.

According to some embodiments of the invention, the crystalline form of perphenazine 4-aminobutyrate trimesylate is characterized by an X-Ray Powder Diffraction (XRPD) pattern exhibiting at least six of the peaks shown in FIG. 2 or one or more of FIGS. 3A-I.

According to some embodiments of the invention, the crystalline form of perphenazine 4-aminobutyrate trimesylate is characterized by an X-Ray Powder Diffraction (XRPD) pattern exhibiting at least seven of the peaks shown in FIG. 2 or one or more of FIGS. 3A-I.

According to some embodiments of the invention, the crystalline form of perphenazine 4-aminobutyrate trimesylate is characterized by an X-Ray Powder Diffraction (XRPD) pattern substantially identical to one or more of the XRPD patterns shown in FIG. 2.

According to some embodiments of the invention, the crystalline form of perphenazine 4-aminobutyrate trimesylate is characterized by an X-Ray Powder Diffraction (XRPD) pattern substantially identical to one or more of the XRPD patterns shown in FIGS. 3A-I.

According to an aspect of some embodiments of the present invention, there is provided a crystalline form of perphenazine 4-aminobutyrate trimesylate characterized by an X-Ray Powder Diffraction (XRPD) pattern exhibiting at least five of the peaks shown in FIG. 2.

According to some embodiments of the invention, the crystalline form of perphenazine 4-aminobutyrate trimesylate is characterized by an X-Ray Powder Diffraction (XRPD) pattern exhibiting at least six or at least seven of the peaks shown in FIG. 2.

According to other embodiments of the invention, the crystalline form of perphenazine 4-aminobutyrate trimesylate is characterized by an X-Ray Powder Diffraction (XRPD) pattern exhibiting at least five of the peaks shown in FIG. 2 selected from the group having 2Θ values (in units of degrees) of about 4.7, 5.4, 6.4, 7.8, 9.4, 10.9, 11.7, 12.8, 14, 15.3, 15.4, 15.7, 16.0, 16.1, 16.9, 17.4, 17.7, 18.0, 18.4, 19.0, 19.7, 20.0, 20.6, 21.0, 21.2, 21.5, 22.3, 23.1, 23.4, 23.6, 23.9, 24.4, 24.8, and 25.0.

According to other embodiments of the invention, the crystalline form of perphenazine 4-aminobutyrate trimesylate is characterized by an X-Ray Powder Diffraction (XRPD) pattern exhibiting at least five of the peaks shown in FIG. 2 selected from the group having 2Θ values (in units of degrees)

of about 4.7, 5.4, 6.4, 7.8, 12.8, 14.0, 15.3, 15.7, 16.0, 16.1, 16.9, 17.7, 18.0, 19.7, 20.0, 20.6, 21.0, and 21.2.

According to other embodiments of the invention, the crystalline form of perphenazine 4-aminobutyrate trimesylate is characterized by an X-Ray Powder Diffraction (XRPD) pattern exhibiting at least six of the peaks shown in FIG. 2 selected from the group having 2Θ values (in units of degrees) of about 4.7, 5.4, 6.4, 7.8, 9.4, 10.9, 11.7, 12.8, 14, 15.3, 15.4, 15.7, 16.0, 16.1, 16.9, 17.4, 17.7, 18.0, 18.4, 19.0, 19.7, 20.0, 20.6, 21.0, 21.2, 21.5, 22.3, 23.1, 23.4, 23.6, 23.9, 24.4, 24.8, and 25.0.

According to other embodiments of the invention, the crystalline form of perphenazine 4-aminobutyrate trimesylate is characterized by an X-Ray Powder Diffraction (XRPD) pattern exhibiting at least six of the peaks shown in FIG. 2 selected from the group having 2Θ values (in units of degrees) of about 4.7, 5.4, 6.4, 7.8, 12.8, 14.0, 15.3, 15.7, 16.0, 16.1, 16.9, 17.7, 18.0, 19.7, 20.0, 20.6, 21.0, and 21.2.

According to other embodiments of the invention, the crystalline form of perphenazine 4-aminobutyrate trimesylate is characterized by an X-Ray Powder Diffraction (XRPD) pattern exhibiting at least seven of the peaks shown in FIG. 2 selected from the group having 2Θ values (in units of degrees) of about 4.7, 5.4, 6.4, 7.8, 9.4, 10.9, 11.7, 12.8, 14, 15.3, 15.4, 15.7, 16.0, 16.1, 16.9, 17.4, 17.7, 18.0, 18.4, 19.0, 19.7, 20.0, 20.6, 21.0, 21.2, 21.5, 22.3, 23.1, 23.4, 23.6, 23.9, 24.4, 24.8, and 25.0.

According to other embodiments of the invention, the crystalline form of perphenazine 4-aminobutyrate trimesylate is characterized by an X-Ray Powder Diffraction (XRPD) pattern exhibiting at least seven of the peaks shown in FIG. 2 selected from the group having 2Θ values (in units of degrees) of about 4.7, 5.4, 6.4, 7.8, 12.8, 14.0, 15.3, 15.7, 16.0, 16.1, 16.9, 17.7, 18.0, 19.7, 20.0, 20.6, 21.0, and 21.2.

According to some embodiments of the invention, the crystalline form of perphenazine 4-aminobutyrate trimesylate is characterized by an X-Ray Powder Diffraction (XRPD) pattern substantially identical to one or more of the XRPD patterns shown in FIG. 2.

According to an aspect of some embodiments of the present invention, there is provided a crystalline form of perphenazine 4-aminobutyrate trimesylate, characterized by an X-Ray Powder Diffraction (XRPD) pattern substantially identical to one or more of the XRPD patterns shown in FIGS. 3A-I.

According to an aspect of some embodiments of the present invention, there is provided a crystalline form of perphenazine 4-aminobutyrate trimesylate characterized by a Differential Scanning Calorimetry (DSC) exhibiting an endothermic peak at or higher than about 209° C. (e.g., being about 214° C.).

According to some embodiments of the invention, the crystalline form of perphenazine 4-aminobutyrate trimesylate has a purity greater than about 95%, as determined by HPLC area percentage measurements. In other embodiments, the purity of the crystalline form of perphenazine 4-aminobutyrate trimesylate is greater than about 96%, greater than about 97%, greater than about 98%, greater than about 99%, or greater than about 99.5%, inclusive of all ranges and subranges therebetween.

According to some embodiments of the invention, the crystalline form of perphenazine 4-aminobutyrate trimesylate has an average particle size smaller than 100 microns (e.g., less than about 95 microns, less than about 90 microns, less than about 85 microns, less than about 80 microns, less than about 75 microns, less than about 70 microns, less than about 65 microns, less than about 60 microns, less than about 55 microns, less than about 50 microns, less than about 45 microns, less than about 40 microns, less than about 35 microns, less than about 30 microns, less than about 25 microns, less than about 20 microns, less than about 15 microns, or less than about 10 microns, inclusive of all ranges and subranges therebetween).

According to some embodiments of the invention, the crystalline form of perphenazine 4-aminobutyrate trimesylate is generally shaped as needles and spherulite fragments exhibiting birefringence with extinction.

According to some embodiments of the invention, the crystalline form of perphenazine 4-aminobutyrate trimesylate is generally shaped as needles.

According to some embodiments of the invention, the crystalline form of perphenazine 4-aminobutyrate trimesylate is characterized by a surface area higher than 2.5 $m^2/g$.

According to some embodiments of the invention, the crystalline form of perphenazine 4-aminobutyrate trimesylate is characterized by a surface area that ranges from 4.5 $m^2/g$ to 5 $m^2/g$.

According to some embodiments of the invention, the crystalline form of perphenazine 4-aminobutyrate trimesylate is prepared by reacting N-protected perphenazine 4-aminobutyrate and methanesulfonic acid, in the presence of a mixture of acetonitrile and butyl acetate as a solvent.

According to an aspect of some embodiments of the present invention, there is provided a crystalline form of perphenazine 4-aminobutyrate trimesylate (crystalline Form A) characterized by a Differential Scanning Calorimetry (DSC) exhibiting an endothermic peak at about 150° C.

According to some embodiments of the invention, this crystalline form of perphenazine 4-aminobutyrate trimesylate is prepared by reacting N-protected perphenazine 4-aminobutyrate and methanesulfonic acid, in the presence of acetonitrile as a solvent.

According to an aspect of some embodiments of the present invention, there is provided a process of preparing the crystalline Form B as described herein, the process comprising reacting an N-protected perphenazine 4-aminobutyrate and methanesulfonic acid, in the presence of a mixture of acetonitrile and butyl acetate as a solvent, thereby producing the crystalline form of perphenazine 4-aminobutyrate trimesylate.

According to some embodiments of the invention, the N-protected perphenazine 4-aminobutyrate comprises t-butoxycarbonyl as an N-protecting group.

According to some embodiments of the invention, the reacting is performed by:
(i) dissolving the N-protected perphenazine 4-aminobutyrate in a mixture of acetonitrile and butyl acetate; and
(ii) adding a solution of methanesulfonic acid in acetonitrile to the solution of the N-protected perphenazine 4-aminobutyrate in the mixture of acetonitrile and butyl acetate.

According to some embodiments of the invention, the solution of the N-protected perphenazine 4-aminobutyrate in the mixture of acetonitrile and butyl acetate is heated to about 40° C.

According to some embodiments of the invention, the process further comprises isolating the crystalline form of perphenazine 4-aminobutyrate trimesylate from the reaction mixture.

According to some embodiments of the invention, the process further comprises purifying the perphenazine 4-aminobutyrate trimesylate salt, for example by recrystallization (e.g., from mixtures of acetonitrile and butyl acetate), trituration, etc.

According to an aspect of some embodiments of the present invention, there is provided a process of preparing perphenazine 4-aminobutyrate trimesylate, the process comprising reacting an N-protected perphenazine 4-aminobutyrate and methanesulfonic acid, in the presence of a mixture of acetonitrile and butyl acetate as a solvent, thereby producing perphenazine 4-aminobutyrate trimesylate.

According to some embodiments of the invention, the perphenazine 4-aminobutyrate trimesylate has a purity higher than 99%, as determined by area percentage in HPLC measurements.

According to some embodiments of the invention, the process is used to prepare a crystalline form of the perphenazine 4-aminobutyrate trimesylate, and provides a crystalline form of the perphenazine 4-aminobutyrate trimesylate characterized by a Differential Scanning Calorimetry (DSC) that exhibits an endothermic peak at or higher than 209° C.

According to an aspect of some embodiments of the present invention, there is provided a perphenazine 4-aminobutyrate trimesylate having a purity higher than 99%, as determined by area percentage in HPLC measurements, prepared by the process as described herein.

According to an aspect of some embodiments of the present invention, there is provided a pharmaceutical composition comprising the crystalline Form B of perphenazine 4-aminobutyrate trimesylate and a pharmaceutically acceptable carrier.

According to some embodiments of the invention, the pharmaceutical composition is packaged in a packaging material and identified in print, in or on the packaging material, for use in the treatment of a CNS disease or disorder.

According to an aspect of some embodiments of the present invention, the crystalline Form B of perphenazine 4-aminobutyrate trimesylate as described herein is for use in the treatment of a CNS disease or disorder.

According to an aspect of some embodiments of the present invention, the crystalline Form B of perphenazine 4-aminobutyrate trimesylate as described herein is for use as a medicament.

According to some embodiments of the invention, the medicament is for the treatment of a CNS disease or disorder.

According to an aspect of some embodiments of the present invention, there is provided a use of the crystalline Form B of perphenazine 4-aminobutyrate trimesylate as described herein, in the preparation of a medicament for the treatment of a CNS disease or disorder.

According to an aspect of some embodiments of the present invention, there is provided a method of treating a CNS disease or disorder, the method comprising administering to a subject in need thereof a therapeutically effective amount of the crystalline Form B of perphenazine 4-aminobutyrate trimesylate as described herein, thereby treating the CNS disease or disorder.

According to some embodiments of the invention, the CNS disease or disorder is Schizophrenia.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
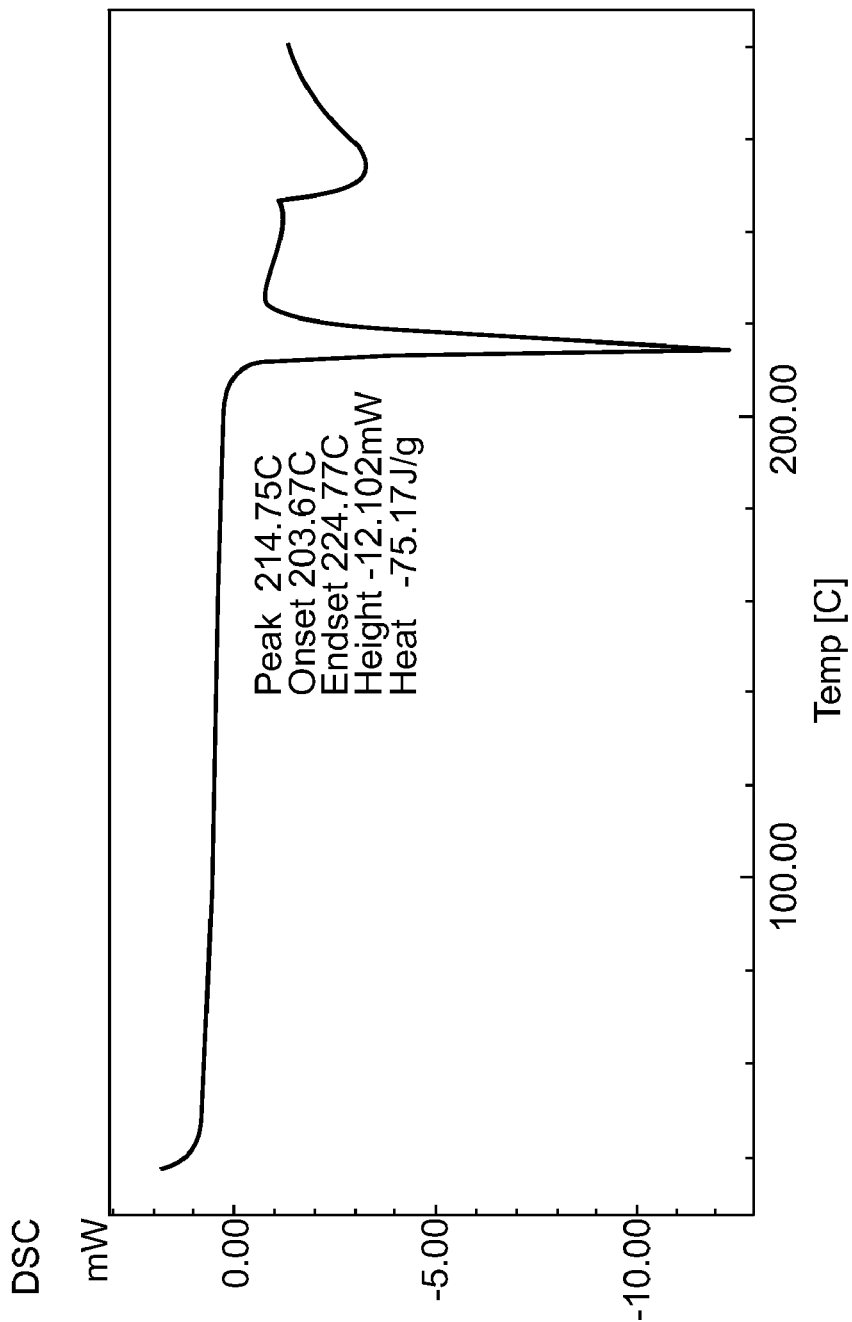
FIG. 1 presents an exemplary DSC curve of crystalline Form B of BL-1020 MSA salt (Lot 06-01915-3), exhibiting an endothermic peak at 214.75° C.

The present invention, in some embodiments thereof, relates to novel crystalline forms of pharmaceutically active agents and, more particularly, but not exclusively, to novel crystalline forms of chemical conjugates comprising a psychotropic drug and an organic acid, to processes of producing same, and to uses thereof in the treatment of CNS diseases and disorders.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Previous publications teach that a conjugate of perphenazine and γ-aminobutyric acid (GABA) exhibits beneficial therapeutic effects and is therefore a promising pharmaceutically active agent.

While further characterizing the trimesylate salt of the perphenazine-GABA conjugate, perphenazine γ-aminobutyrate trimesylate, also referred to herein and in the art as perphenazine 4-aminobutyrate trimesylate or BL-1020 MSA salt or trimesylate salt of perphenazine 4-aminobutyrate, the present inventors have discovered that depending on the reaction conditions used for preparing a trimesylate salt of a perphenazine-GABA conjugate, various crystalline forms of the salt are obtained. The present inventors have therefore designed a process of preparing a crystalline form of a trimesylate salt of a perphenazine-GABA conjugate, which exhibits higher purity and stability, compared to trimesylate salts prepared under other conditions. The present inventors have further characterized the highly stable crystalline form uncovered.

A trimesylate salt of perphenazine 4-aminobutyrate was prepared by reacting N-protected perphenazine 4-aminobutyrate and methanesulfonic acid in the presence of acetonitrile as a solvent (e.g., using the method of WO 2006/131923). Differential Scanning Calorimetry (DSC) analysis has shown that a sharp endothermic peak is exhibited at about 150° C., suggesting that the product is crystalline. This product is referred to herein as Crystalline Form A of perphenazine 4-aminobutyrate trimesylate.

While exploring the effect of the reaction conditions on the formed trimesylate salts, the present inventors have uncovered that by using a mixture of acetonitrile and butyl acetate as the reaction solvent, a product that exhibits higher purity, higher melting temperature and higher stability is formed. The product obtained by the process described herein was further characterized and was found to be single crystalline, and to therefore exhibit a unique XRD pattern and other characteristic features. This product is referred to herein as Crystalline Form B of perphenazine 4-aminobutyrate trimesylate.

General techniques for the crystallization of compounds are known to those skilled in the art. Such techniques include, for example, crystallization from solvents, thermal treatment and sublimation. It is not possible to know, a priori and without extensive experimentation, which procedure, process or regime will provide good crystallization of a given compound. Further, it is not known how many different crystalline forms a given compound may have.

Generally, the crystalline forms of perphenazine 4-aminobutyrate trimesylate are prepared in situ, by reacting an N-protected perphenazine 4-amino butyrate (in which the amino group is protected by an N-protecting group), with methanesulfonic acid (MSA), in a solvent or a mixture of solvents, in a single-step synthesis where deprotection of the N-protected perphenazine 4-amino butyrate and salification (formation of the MSA addition salt) are effected substantially concomitantly. The type of crystalline form that is produced may be influenced by the solvent or mixture of solvents used in the reaction.

Thus, according to an aspect of some embodiments of the present invention, there is provided a crystalline form of perphenazine 4-aminobutyrate trimesylate (Crystalline Form B), characterized by at least one of:
  (a) an X-Ray Powder Diffraction (XRPD) pattern exhibiting at least five of the peaks depicted in FIG. 2;
  (b) an X-Ray Powder Diffraction (XRPD) pattern exhibiting at least five of the peaks depicted in FIG. 2, selected from peaks having 2Θ values (in units of degrees) of about 4.7, 5.4, 6.4, 7.8, 9.4, 10.9, 11.7, 12.8, 14, 15.3, 15.4, 15.7, 16.0, 16.1, 16.9, 17.4, 17.7, 18.0, 18.4, 19.0, 19.7, 20.0, 20.6, 21.0, 21.2, 21.5, 22.3, 23.1, 23.4, 23.6, 23.9, 24.4, 24.8, and 25.0.
  (c) a Differential Scanning Calorimetry (DSC) exhibiting an endothermic peak at or higher than about 209° C.

In some embodiments, there is provided a crystalline form of perphenazine 4-aminobutyrate trimesylate (Crystalline Form B), characterized by a Differential Scanning Calorimetry (DSC) exhibiting an endothermic peak at or higher than about 209° C.

Figure 2:
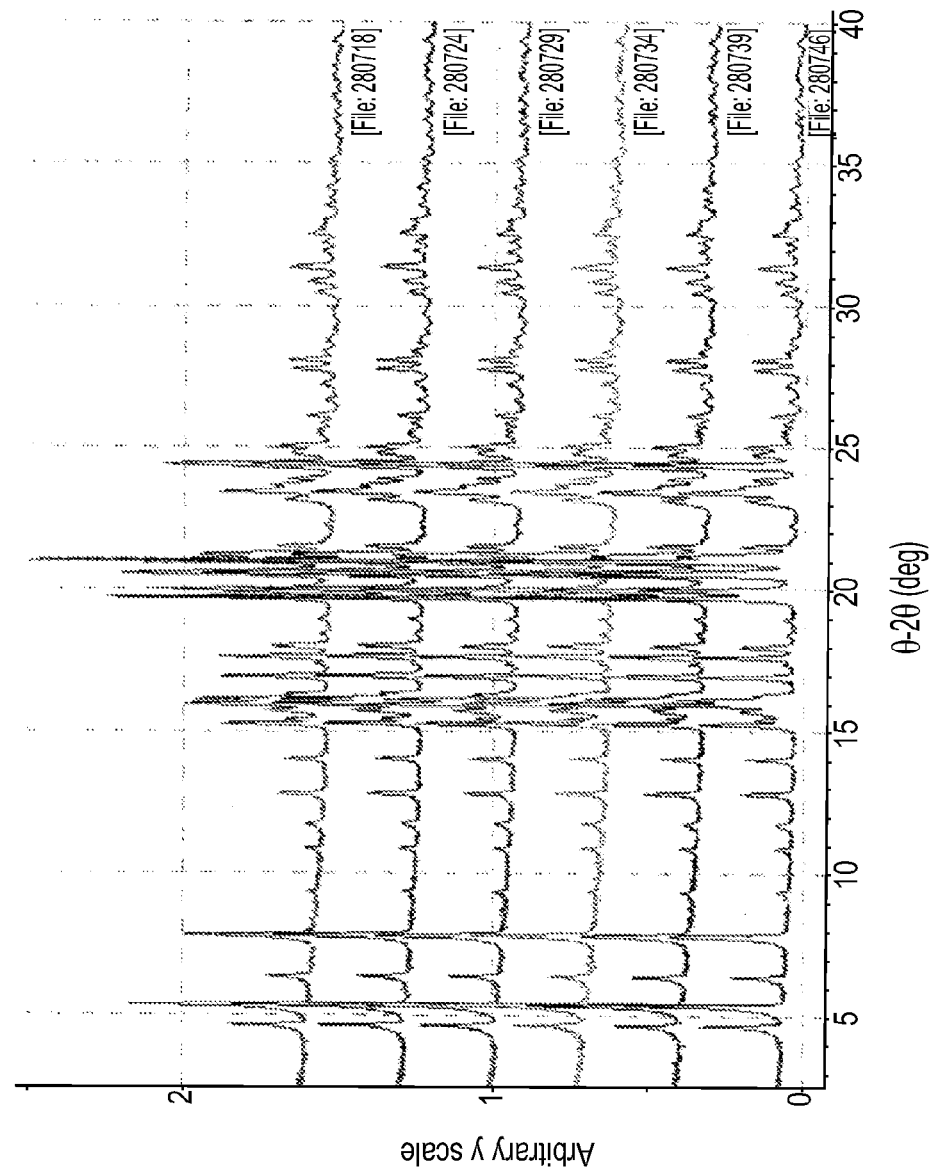
FIG. 2 presents an overlay of XRPD patterns obtained for exemplary Lots 06-01915-3; 01BIL02-01-22; 01BIL02-02-22; 01BIL02-03-22; 01BIL02-04-22; and 01BIL02-05-26, corresponding to files 280718, 280714, 280729, 280734, 280739 and 280746, respectively, of crystalline Form B of BL-2010 MSA salt.

In some embodiments, there is provided a crystalline form of perphenazine 4-aminobutyrate trimesylate (Crystalline Form B), characterized by an X-Ray Powder Diffraction (XRPD) pattern exhibiting at least five of the peaks depicted in FIG. 2.

In some embodiments, there is provided a crystalline form of perphenazine 4-aminobutyrate trimesylate (Crystalline Form B), characterized by an X-Ray Powder Diffraction (XRPD) pattern exhibiting at least five of the peaks depicted in FIG. 2, selected from peaks having 2Θ values (in units of degrees) of about 4.7, 5.4, 6.4, 7.8, 9.4, 10.9, 11.7, 12.8, 14, 15.3, 15.4, 15.7, 16.0, 16.1, 16.9, 17.4, 17.7, 18.0, 18.4, 19.0, 19.7, 20.0, 20.6, 21.0, 21.2, 21.5, 22.3, 23.1, 23.4, 23.6, 23.9, 24.4, 24.8, and 25.0.

In some embodiments, there is provided a crystalline form of perphenazine 4-aminobutyrate trimesylate (Crystalline Form B), characterized by an X-Ray Powder Diffraction (XRPD) pattern exhibiting at least five of the peaks depicted in FIG. 2, selected from peaks having 2Θ values (in units of degrees) of about 4.7, 5.4, 6.4, 7.8, 12.8, 14.0, 15.3, 15.7, 16.0, 16.1, 16.9, 17.7, 18.0, 19.7, 20.0, 20.6, 21.0, and 21.2.

In some embodiments, there is provided a crystalline form of perphenazine 4-aminobutyrate trimesylate (Crystalline Form B), characterized by both an X-Ray Powder Diffraction (XRPD) pattern exhibiting at least five of the peaks depicted in FIG. 2, selected from peaks having 2Θ values (in units of degrees) of about 4.7, 5.4, 6.4, 7.8, 9.4, 10.9, 11.7, 12.8, 14, 15.3, 15.4, 15.7, 16.0, 16.1, 16.9, 17.4, 17.7, 18.0, 18.4, 19.0, 19.7, 20.0, 20.6, 21.0, 21.2, 21.5, 22.3, 23.1, 23.4, 23.6, 23.9, 24.4, 24.8, and 25.0; and a Differential Scanning calorimetry (DSC) exhibiting an endothermic peak at or higher than about 209° C.

In some embodiments, there is provided a crystalline form of perphenazine 4-aminobutyrate trimesylate (Crystalline Form B), characterized by both an X-Ray Powder Diffraction (XRPD) pattern exhibiting at least five of the peaks depicted in FIG. 2, selected from peaks having 2Θ values (in units of degrees) of about 4.7, 5.4, 6.4, 7.8, 12.8, 14.0, 15.3, 15.7, 16.0, 16.1, 16.9, 17.7, 18.0, 19.7, 20.0, 20.6, 21.0, and 21.2; and a Differential Scanning Calorimetry (DSC) exhibiting an endothermic peak at or higher than about 209° C.

In some embodiments, there is provided a crystalline form of perphenazine 4-aminobutyrate trimesylate (Crystalline Form B), characterized by both an X-Ray Powder Diffraction (XRPD) pattern exhibiting at least five of the peaks depicted in FIG. 2, and a Differential Scanning Calorimetry (DSC) exhibiting an endothermic peak at or higher than about 209° C.

In some embodiments, the endothermic peak is at about 214° C.

As used herein in the context of "endothermic peak", the term "about" describes ±10% or ±5%.

It is to be noted that the data obtained in DSC measurements depend in part on the instrument used and the environmental conditions at the time measurements are carried out (e.g., humidity). It is to be also noted that the value of an endothermic peak described herein refers to the maximal value observed, while in effect, peak onset can be between 10 and 20° C. lower.

Accordingly, an endothermic peak of Crystalline Form B can be, for example, at any value ranging from 190° C. to 230° C., and thus can be, for example, 195° C., 200° C., 205° C., 206° C., 207° C., 208° C., 209° C., 210° C., 211° C., 212° C., 213° C., 214° C., 215° C., 216° C., 217° C., 218° C., 219° C. or 220° C. Other values within the range of values indicated herein are also contemplated, as well as ranges and subranges between any of these values.

As described in the Examples section that follows, various samples of a perphenazine 4-aminobutyrate trimesylate, all prepared under the same synthetic conditions, were subjected to XRPD measurements and all exhibited similar XRPD patterns, which were therefore defined as characteristic of a single crystalline form.

As known is the art, each crystalline form of a substance has a characteristic XRPD pattern and equivalency can therefore be determined if substances exhibit XRPD patterns that have at least some of the positional peaks and corresponding relative intensities substantially identical.

Representative XRPD patterns of crystalline Form B as described herein are depicted in FIG. 2 and in FIGS. 3A-I.

In some embodiments, the crystalline form of perphenazine 4-aminobutyrate trimesylate is characterized by an X-Ray Powder Diffraction (XRPD) pattern exhibiting at least five, six, seven or more of the peaks depicted in FIG. 2, for example five, six, seven or more of the peaks having 2Θ values (in units of degrees) of about 4.7, 5.4, 6.4, 7.8, 9.4, 10.9, 11.7, 12.8, 14, 15.3, 15.4, 15.7, 16.0, 16.1, 16.9, 17.4, 17.7, 18.0, 18.4, 19.0, 19.7, 20.0, 20.6, 21.0, 21.2, 21.5, 22.3, 23.1, 23.4, 23.6, 23.9, 24.4, 24.8, and 25.0.

Reference to the peaks depicted in FIG. 2 is made for the peak position, namely, for the refraction angle (2Θ) at which a peak is observed. Optionally, reference is made also for the relative intensity of a peak observed at a refraction angle.

In some embodiments, the crystalline form of perphenazine 4-aminobutyrate trimesylate is characterized by an X-Ray Powder Diffraction (XRPD) pattern substantially identical to one or more of the XRPD patterns depicted in FIG. 2.

In some embodiments, a crystalline form of perphenazine 4-aminobutyrate trimesylate is characterized by an X-Ray Powder Diffraction (XRPD) pattern substantially identical to one or more of the XRPD patterns depicted in FIGS. 3A-3F.

In some embodiments, the crystalline form of perphenazine 4-aminobutyrate trimesylate described in the context of these embodiments (e.g., Form B) has a purity of at least about 95%, or greater than about 96%, greater than about 97%, greater than about 98%, greater than about 99%, greater than about 99.1%, greater than about 99.2%, greater than about 99.3%, greater than about 99.4%, greater than about 99.5%, greater than about 99.6%, greater than about 99.7%, greater than about 99.8%, or greater than about 99.9%, or about 100% as determined by HPLC area percentage measurements.

By "HPLC area percentage measurements" it is meant the area percentage of a peak that is identified as corresponding to perphenazine 4-aminobutyrate trimesylate. This term does necessarily refer to values obtained when performing quantity analysis using HPLC measurements.

As described in detail in the Examples section that follows, several samples of the crystalline form of perphenazine 4-aminobutyrate trimesylate described in the context of these embodiments have been analyzed also for their moisture absorption/desorption (DVS), BET surface area, particle size, and characterized by light microscopy. Most of the tested samples were found to exhibit similar physicochemical characterizing features.

In some embodiments, the average particle size of the crystalline form of perphenazine 4-aminobutyrate trimesylate described in the context of these embodiments is smaller than 100 microns, and can optionally be smaller than 50 microns, smaller than 40 microns, smaller than 30 microns, smaller than 20 microns and smaller than 10 microns. In particular embodiments, the mean particle size is between about 1 micron and about 100 microns. In other embodiments, the mode of the particle size distribution is between about 1 micron and about 50 microns, for example about 1 micron, about 5 microns, about 10 microns, about 15 microns, about 20 microns, about 25 microns, about 30 microns, about 35 microns, about 40 microns, about 45 microns, or about 50 microns, inclusive of all ranges and subranges therebetween.

In some embodiments, the average particle size of the crystalline form of perphenazine 4-aminobutyrate trimesylate described in the context of these embodiments ranges from 4 to 10 microns.

In some embodiments, the particle size distribution is substantially unimodal.

In some embodiments, the particle size and the particle size distribution are determined as described in the Examples section that follows.

In some embodiments, the crystalline form of perphenazine 4-aminobutyrate trimesylate described in the context of these embodiments is generally shaped as needles and spherulite fragments, as determined by light microscopy.

In some embodiments, these fragments exhibit birefringence with extinction.

In some embodiments, the crystalline form of perphenazine 4-aminobutyrate trimesylate described in the context of these embodiments is generally shaped as needles.

In some embodiments, the surface area of the crystalline form of perphenazine 4-aminobutyrate trimesylate described in the context of these embodiments is higher than about 2.5 $m^2/g$.

In some embodiments, the surface area ranges from 4.5 $m^2/g$ to 5 $m^2/g$. In other embodiments, the surface area ranges from about 2.5 $m^2/g$ to 5 $m^2/g$.

In some embodiments, the surface area is determined by BET measurements, such as, for example, those described in the Examples section that follows.

In some embodiments, the density of the crystalline form of perphenazine 4-aminobutyrate trimesylate described in the context of these embodiments ranges from about 0.1 to about 0.2 g/mL (bulk) or about 0.2 to about 0.3 g/mL (tapped). The density can be measured by methods well known in the art.

According to some embodiments, crystalline Form B of perphenazine 4-aminobutyrate trimesylate as described herein is prepared by reacting N-protected perphenazine 4-aminobutyrate and methanesulfonic acid, in the presence of a mixture of acetonitrile and butyl acetate as a solvent, as described in further detail herein.

As noted herein, it has been discovered that perphenazine 4-aminobutyric acid trimesylate is polymorphic, and thus can exhibit two or more crystalline forms (isomorphs).

According to an aspect of some embodiments of the present invention, there is provided a crystalline form of perphenazine 4-aminobutyrate trimesylate (crystalline Form A), which is characterized by a Differential Scanning Calorimetry (DSC) exhibiting an endothermic peak at about 150° C. Crystalline Form A is thus characterized by a DSC with a lower endothermic peak, compared to crystalline Form B as described herein.

Figure 6A:
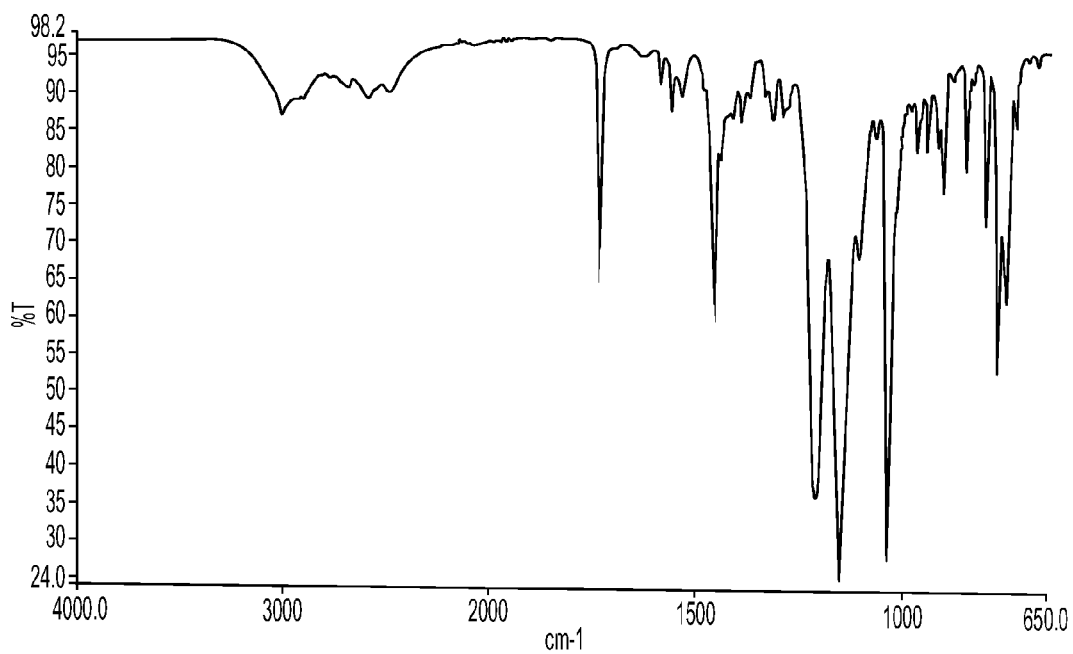
FIGS. 6A-B present FT-IR spectra of crystalline form B of BL-2010 MSA salt (Lot CYS02-01-37) and reference sample 06-01890MC4-2.
Figure 6B:
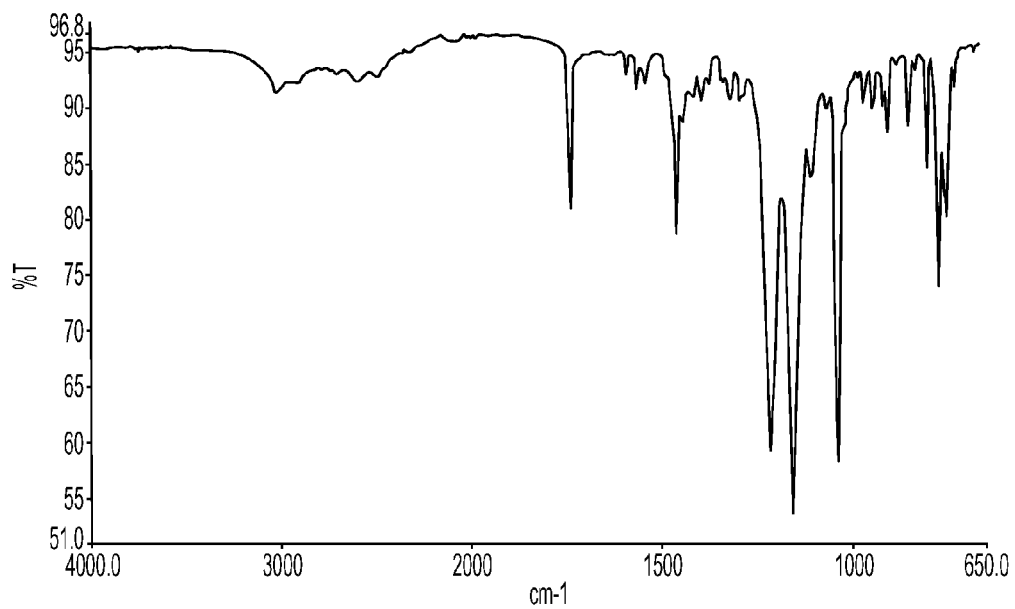

According to other embodiments of the present invention, the crystalline form of perphenazine 4-aminobutyrate trimesylate (crystalline Form B) is characterized by an FT-IR spectrum as shown in FIG. 6A. The spectrum is obtained by applying a small amount of the crystalline Form B of perphenazine 4-aminobutyrate trimesylate onto an ATR crystal with application of sufficient pressure to maintain contact between the sample and the ATR crystal. The FT-IR spectrum was obtained by conventional methods, providing the spectrum shown in FIG. 6. The spectrum shows strong absorptions at about 1209 $cm^{-1}$, 1151 $cm^{-1}$, and 1036 $cm^{-1}$; medium absorptions at 1736 $cm^{-1}$, 1459 $cm^{-1}$, 802 $cm^{-1}$, and 771 cm$^{-1}$; and weak absorptions at 3012 cm$^{-1}$, 2696-2492 cm$^{-1}$ (broad), 1590 cm$^-$, 1564 cm$^{-1}$, 1541 cm$^{-1}$, 969 cm$^{-1}$, 945 cm$^{-1}$, 918 cm$^{-1}$, 906 cm$^{-1}$, and 851 cm$^{-1}$.

In some embodiments, crystalline Form A is prepared by reacting N-protected perphenazine 4-aminobutyrate and methanesulfonic acid, in the presence of acetonitrile as a solvent.

The crystalline forms of perphenazine 4-aminobutyrate trimesylate disclosed herein, referred to herein as Crystalline Forms A and B, may optionally contain unnatural proportions of atomic isotopes at one or more of the atoms that constitute such compounds. For example, the crystalline forms of perphenazine 4-aminobutyrate trimesylate described herein may be radiolabeled with radioactive isotopes, such as for example tritium ($^3$H) or carbon-14 ($^{14}$C). All isotopic variations of the compounds of the present invention, whether radioactive or not, are intended to be encompassed within the scope of the present invention.

In some embodiments, crystalline Form B, in addition to exhibiting a DSC with an endothermic peak at a higher temperature as compared to crystalline Form A, was further found to exhibit higher stability and reduced hygroscopy. In addition, the process used for obtaining crystalline Form B as described herein resulted in perphenazine 4-aminobutyrate trimesylate of a purity higher than that obtained in the process used for obtaining crystalline Form A.

According to an aspect of some embodiments of the present invention there is provided a process of preparing Crystalline Form B of perphenazine 4-aminobutyrate trimesylate as described herein. The process is effected by reacting an N-protected perphenazine 4-aminobutyrate and methanesulfonic acid, in the presence of a solvent, whereby the solvent is a mixture of acetonitrile and butyl acetate.

By "N-protected perphenazine 4-aminobutyrate" it is meant that the free amino group that is derived from GABA is protected by an N-protecting group (e.g., an amino protecting group). Selecting a suitable N-protecting group is performed while considering the synthetic steps involved in the process, the reagents used and the reaction conditions, and is well within the knowledge of a person skilled in the art.

In some embodiments, the N-protecting group is t-butoxycarbonyl (t-BOC), such that the N-protected perphenazine 4-aminobutyrate comprises t-butoxycarbonyl as an N-protecting group.

An N-protected perphenazine 4-aminobutyrate can be readily prepared by reacting perphenazine and N-protected GABA, in the presence of a coupling reagent such as dicyclohexylcarbodiimide (DCC), under conditions for promoting esterification. An exemplary procedure is described in detail in the Examples section that follows.

In some embodiments, reacting the N-protected perphenazine 4-aminobutyrate and the methanesulfonic acid is performed by:
(i) dissolving the N-protected perphenazine 4-aminobutyrate in a mixture of acetonitrile and butyl acetate; and
(ii) adding a solution of methanesulfonic acid in acetonitrile to the solution of the N-protected perphenazine 4-aminobutyrate in the mixture of acetonitrile and butyl acetate.

In some embodiments, the mixture of acetonitrile and butyl acetate comprises from 40% to 60% by volume acetonitrile, for example about 40 volume % acetonitrile, about 45 volume % acetonitrile, about 50 volume % acetonitrile, about 55 volume % acetonitrile, or about 60 volume % acetonitrile, inclusive of all ranges and subranges therebetween. In some embodiments, the mixture is a 1:1 acetonitrile:butyl acetate mixture (by volume).

In some embodiments a 1:1 acetonitrile:butyl acetate mixture (by volume) is obtained upon addition of the solution of MSA in acetonitrile.

In some embodiments, dissolving the N-protected perphenazine 4-aminobutyrate in a mixture of acetonitrile and butyl acetate is effected by mixing the N-protected perphenazine 4-aminobutyrate in butyl acetate and then adding acetonitrile, optionally while heating the mixture (e.g., to about 40° C.).

In some embodiments, the solution of the N-protected perphenazine 4-aminobutyrate in the mixture of acetonitrile and butyl acetate is heated to about 40° C., during the addition of MSA. Optionally, the reaction mixture obtained upon the addition of MSA is further heated at about 40° C., for several hours (e.g., from 10 to 30 hours).

As noted herein, reacting the N-protected perphenazine 4-aminobutyrate with MSA under the described conditions results in both deprotection of the N-protecting group so as to produce a free base form of perphenazine 4-aminobutyrate, and salification, namely, formation of the trimesylate acid addition salt product.

In some embodiments, once the reaction is completed, the formed of perphenazine 4-aminobutyrate trimesylate is isolated from the reaction mixture.

In some embodiments, isolating is effected by cooling the reaction mixture and filtering the solid product. Optionally, the solid product is thereafter subjected to a drying procedure.

In some embodiments, the crystalline Form B of perphenazine 4-aminobutyrate trimesylate as described herein is obtained by the process as described herein, in a purity higher than about 99%, as determined by area percentage in HPLC measurements, as defined herein.

The above described process can therefore be used for preparing perphenazine 4-aminobutyrate trimesylate of high purity.

According to an aspect of some embodiments of the present invention there is provided a process of preparing perphenazine 4-aminobutyrate trimesylate, the process comprising reacting an N-protected perphenazine 4-aminobutyrate and methanesulfonic acid, as described herein, in the presence of a mixture of acetonitrile and butyl acetate as a solvent, as described herein.

In some embodiments, the process according to embodiments of this aspect of the present invention is used for preparing highly pure perphenazine 4-aminobutyrate trimesylate.

In some embodiments, the process is for preparing a crystalline form of the perphenazine 4-aminobutyrate trimesylate, which is characterized by a Differential Scanning Calorimetry (DSC) that exhibits an endothermic peak at or higher than about 209° C. (e.g., being crystalline Form B of perphenazine 4-aminobutyrate trimesylate, as described herein).

In some embodiments, the obtained solid product is further subjected to purification.

In some embodiments, purification is effected by recrystallizing the solid product in a mixture of acetonitrile and butyl acetate, substantially identical to the mixture used while reacting the N-protected of perphenazine 4-aminobutyrate trimesylate and MSA.

In some embodiments, the perphenazine 4-aminobutyrate trimesylate obtained by any of the processes described herein has a purity higher than about 99%, as determined by area percentage in HPLC measurements.

According to an aspect of some embodiments of the present invention, there is provided a highly pure perphenazine 4-aminobutyrate trimesylate, prepared by the process described hereinabove.

In some embodiments, the perphenazine 4-aminobutyrate trimesylate obtainable by this process has a purity higher than about 99%, as determined by area percentage in HPLC measurements The physicochemical properties of crystalline Form B of perphenazine 4-aminobutyrate trimesylate described herein render it highly suitable for use as a pharmaceutical active agent.

In some embodiments, the crystalline Form B of perphenazine 4-aminobutyrate trimesylate, as described herein, is identified for use as a medicament.

In some embodiments, the crystalline Form B of perphenazine 4-aminobutyrate trimesylate, as described herein, is identified for use in the treatment of a CNS (Central Nervous System) disease or disorder, as is further detailed herein.

According to an aspect of some embodiments of the present invention, there is provided a use of the crystalline Form B of perphenazine 4-aminobutyrate trimesylate, as described herein, in the manufacture of a medicament.

In some embodiments, the medicament is for the treatment of a CNS disease or disorder, as is further detailed herein.

According to an aspect of some embodiments of the present invention, there is provided a method of treating a CNS disease or disorder in a subject in need thereof, the process comprising administering to the subject a therapeutically effective amount of the crystalline Form B of perphenazine 4-aminobutyrate trimesylate, as described herein.

The crystalline Form B of perphenazine 4-aminobutyrate trimesylate, as described herein, can be used per se, or as a par of a pharmaceutical composition.

According to an aspect of some embodiments of the present invention, there is provided a pharmaceutical composition which comprises crystalline Form B of perphenazine 4-aminobutyrate trimesylate, as described herein, and a pharmaceutically acceptable carrier.

As used herein a "pharmaceutical composition" refers to a preparation of the perphenazine 4-aminobutyrate trimesylate described herein (as active ingredient), with other chemical components including but not limited to physiologically suitable carriers, excipients, lubricants, buffering agents, antibacterial agents, bulking agents (e.g. mannitol), antioxidants (e.g., ascorbic acid or sodium bisulfite), anti-inflammatory agents, anti-viral agents, chemotherapeutic agents, anti-histamines and the like. The purpose of a pharmaceutical composition is to facilitate administration of a compound to a subject. The term "active ingredient" refers to a compound, which is accountable for a biological effect.

The terms "physiologically acceptable carrier" and "pharmaceutically acceptable carrier" which may be used interchangeably refer to a carrier or a diluent that does not cause significant irritation to an organism and does not abrogate the biological activity and properties of the administered compound.

Herein the term "excipient" refers to an inert substance added to a pharmaceutical composition to further facilitate administration of a drug. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., 21$^{st}$ Edition, which is incorporated herein by reference.

Pharmaceutical compositions for use in accordance with the present invention thus may be formulated in conventional manner using one or more pharmaceutically acceptable carriers comprising excipients and auxiliaries, which facilitate processing of the compounds into preparations which can be used pharmaceutically. Proper formulation is dependent upon the route of administration chosen. The dosage may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p. 1).

The pharmaceutical composition may be formulated for administration in either one or more of routes depending on whether local or systemic treatment or administration is of choice, and on the area to be treated. Administration may be done orally, by inhalation, or parenterally, for example by intravenous drip or intraperitoneal, subcutaneous, intramuscular or intravenous injection, or topically (including ophthalmically, vaginally, rectally, intranasally).

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The amount of a composition to be administered will, of course, be dependent on the subject being treated, the severity of the affliction, the manner of administration, the judgment of the prescribing physician, etc.

The pharmaceutical composition may further comprise additional pharmaceutically active or inactive agents such as, but not limited to, an anti-bacterial agent, an antioxidant, a buffering agent, a bulking agent, a surfactant, an anti-inflammatory agent, an anti-viral agent, a chemotherapeutic agent and an anti-histamine.

According to an embodiment of the present invention, the pharmaceutical composition described hereinabove is packaged in a packaging material and identified in print, in or on the packaging material, for use in the treatment of a CNS disease or disorder, as described herein.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

The crystalline form of perphenazine 4-aminobutyrate trimesylate as described herein can be used in the treatment of any CNS disease or disorder that is treatable by perphenazine 4-aminobutyrate or a salt thereof.

Such diseases and disorders include, but are not limited to, those described in WO 03/026563, WO 2005/092392, WO 2006/131923 and in U.S. Pat. No. 7,544,681, which are incorporated by reference as if fully set forth herein.

In some embodiments, the crystalline form of perphenazine 4-aminobutyrate trimesylate as described herein can be used in the treatment of Schizophrenia.

In some embodiments, the crystalline form of perphenazine 4-aminobutyrate trimesylate as described herein can be used for improving a cognitive function in a subject in need thereof, as described, for example, in PCT/IL2010/001041 and U.S. patent application Ser. No. 12/963,959, which are incorporated by reference as if fully set forth herein.

In some embodiments, the crystalline form of perpenazine 4-aminobutyrate trimesylate as described herein can be used for the treatment of a subject that has a cognitive impairment or dysfunction. In some exemplary embodiments, the subject is afflicted with a disease or disorder selected from the group consisting of a bipolar disorder, Alzheimer's disease, Huntington's disease, dementia, age-related cognitive decline, mild cognitive impairment, multiple sclerosis, Parkinson's disease, stroke, epilepsy, brain injury, chronic fatigue syndrome, fibromyalgia syndrome, memory loss, a memory deficit, a memory deficit related to brain injury or a post-stroke event, a learning deficiency, cognitive impairment associated with schizophrenia, psychosis, attention deficit disorder (ADHD), mood and affective disorders, amyotrophic lateral sclerosis, borderline personality disorder, behavioral and cognitive problems associated with brain tumors, AIDS dementia complex, dementia associated with Down's syndrome, dementia associated with Lewy Bodies, depression, general anxiety disorder, Tourette's syndrome, TNF-α related conditions, rheumatoid arthritis, rheumatoid spondylitis, muscle degeneration, Paget's disease, gouty arthritis, inflammatory bowel disease, adult respiratory distress syndrome (ARDS), Crohn's disease, rhinitis, ulcerative colitis, anaphylaxis, asthma, Reiter's syndrome, tissue and mental retardation.

In some other exemplary embodiments, the subject is afflicted with a disease or disorder selected from the group consisting of age-related cognitive decline, mild cognitive impairment, multiple sclerosis, stroke, brain injury, chronic fatigue syndrome, fibromyalgia syndrome, memory loss, a memory deficit, a memory deficit related to brain injury or a post-stroke event and a learning deficiency.

In some other embodiments, the crystalline form of perphenazine 4-aminobutyrate trimesylate as described herein can be used to treat a subject who is treated with a CNS-acting drug and is identified, following treatment with said CNS-acting drug, as having a cognitive impairment or dysfunction.

In some other embodiments, the crystalline form of perphenazine 4-aminobutyrate trimesylate as described herein can be used to prevent onset or inhibit progression of a cognitive impairment or dysfunction, e.g., the crystalline form can be administered to a subject having a predisposition for developing a cognitive impairment or dysfunction or has developed certain symptoms, e.g., early signs of cognitive impairment or dysfunction.

Embodiments of the present invention further relate to uses of any of the crystalline form of perphenazine 4-aminobutyrate trimesylate described herein (e.g., crystalline Form A, and crystalline Form B) as medicaments.

Embodiments of the present invention further relate to uses of any of the perphenazine 4-aminobutyrate trimesylate described herein in the treatment of proliferative diseases or disorders, as described in WO 03/026563, WO 2005/092392, WO 2006/131923 and in U.S. Pat. No. 7,544,681.

As used herein the term "about" in conjunction with numerical values or ranges refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating", and any grammatical diversion thereof, includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Synthesis of a Trimesylate Salt of perphenazine-γ-butyrate Using Acetonitrile as a Solvent A trimesylate salt of perphenazine 4-aminobutyrate was prepared as described in WO 2006/131923. DSC measurements showed an endothermic peak at 150.2° C., suggesting that the product is crystalline. The product exhibited a purity of 97.91%, as determined by HPLC area percentage measurements. The product is referred to herein interchangeably as BL1020 MSA salt Crystalline Form A and crystalline Form A of perphenazine 4-aminobutyrate trimesylate.

Example 2

Synthesis of a Trimesylate Salt of perphenazine-γ-butyrate Using a Mixture of Acetonitrile and Butyl Acetate as a Solvent Scheme 1 below presents the synthetic pathway used according to some embodiments of the invention to produce a trimesylate salt of perphenazine 4-aminobutyrate (BL-1020).

Scheme 1

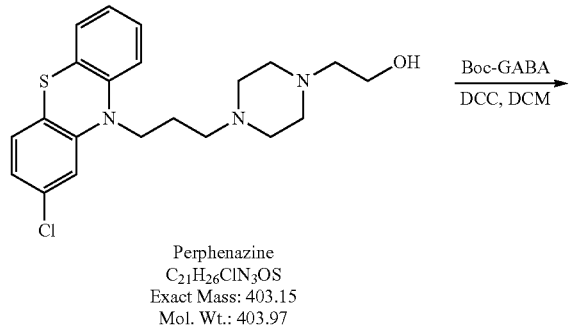

Perphenazine
$C_{21}H_{26}ClN_3OS$
Exact Mass: 403.15
Mol. Wt.: 403.97

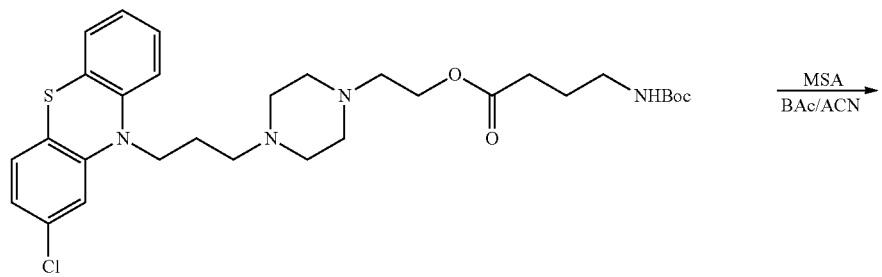

AN-197
$C_{30}H_{41}ClN_4O_4S$
Exact Mass: 588.26
Mol. Wt.: 589.19

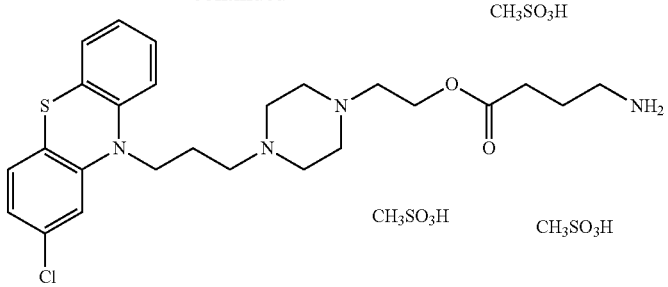

BL-1020
$C_{28}H_{45}ClN_4O_{11}S_4$
Exact Mass: 776.17
Mol. Wt.: 777.39

The product obtained in this process is referred to herein interchangeably as BL-1020 MSA salt crystalline Form B and crystalline Form B of perphenazine 4-aminobutyrate trimesylate.

Analytical Measurements:

HPLC measurements were performed using a Phenomenex Luna C18 (2) column; Column temperature of 40° C.; mobile phase of 0.1% FA in $H_2O$ (A); and acetonitrile (B); Flow rate of 0.5 ml/minute; Detector wavelength of 254 nm; Total run time of 20 minutes.

Differential Scanning calorimetry (DSC) was performed according to USP <891> using a Shimadzu DSC-50 instrument. The DSC was performed under a nitrogen stream by ramping 1-5 mg of samples up to 280° C. at a ramp rate of 10° C. per minute.

Determination of ROI (Residue On Ignition): About 1 mL sulfuric acid was added to the tested sample in a crucible. The sample was burned until no more white fumes evolved. The crucible was placed in an oven at 600° C. overnight or until all carbon was consumed, and was thereafter cooled in a desiccator.

The heavy metals content was determined using USP 29 Supplement 2 <231> Method II.

The amount of residual solvents was determined by GC analyses, using calibration curves.

The ion content of methanesulfonic acid and chloride was determined by ion chromatography-suppressed conductivity.

Preparation of N-Protected perphenazine-γ-aminobutyrate (AN-197):

Perphenazine is reacted with Boc-protected GABA using the following general procedure:

A 3-neck round bottom flask equipped with a thermal well, mechanical stirrer and nitrogen bubbler is charged with perphenazine and anhydrous dichloromethane (DCM) and the mixture is stirred. 4-Dimethylaminopyridine (DMAP) is then added, followed by addition of Boc-GABA, and the reaction mixture is cooled to 0±10° C., using a mixture of ice/water/salt as a cooling bath. DCC as a solution in DCM, is then added over 5 minutes, the cooling bath is removed and the obtained cloudy yellow solution is maintained at room temperature while stirring overnight and monitoring the reaction completion by HPLC. Once the reaction is completed, the reaction mixture is cooled to 0±5° C. and stirred for at least 3 hours to precipitate dicyclohexylurea (DCU). The solids are then filtered and washed twice with DCM, the filtrates are combined and concentrated under reduced pressure (on a rotavap). The residue is then dissolved in ethyl acetate (EtOAc), the solution is cooled to 5±5° C., stirred for at least one hour and then filtered and washed with EtOAc. The filtrate is transferred to a separatory funnel and washed with 5% citric acid (×2), 1M sodium bicarbonate (×2) and brine (×2). The organic layer is concentrated in vacuum and acetonitrile (ACN) is added, followed by agitation at 50° C. until a homogeneous solution is obtained. The solution is transferred to 3-necked round bottom flask, equipped with mechanical stirrer, thermal well and nitrogen bubbler, using ACN. The solution is cooled to 20±5° C., at which time solids begins to form, and is stirred for 1 hour. The solution is then cooled to 10±5° C. and stirred for 1.5±0.5 hours. The obtained solids are then filtered, washed with cold ACN and air-dried for at least 30 minutes. The solids are then transferred to drying trays and dried at 35±5° C. under vacuum until constant weight, to give AN-197 as a yellow solid.

In an exemplary procedure, a 12 L 3-neck round bottom flask equipped with a thermal well, mechanical stirrer and nitrogen bubbler was charged with perphenazine (1.15 Kg, 2.80 mol, 1.0 equivalent) and anhydrous DCM (5.4 L) and the mixture was stirred. A clear, pale yellow solution was obtained. DMAP (0.10 Kg, 0.82 mol, 0.3 equivalent) was then added, followed by addition of Boc-GABA (0.70 Kg, 3.3 mol, 1.2 equivalents), and the reaction mixture was cooled to 0±10° C., using a mixture of ice/water/salt as a cooling bath. DCC (0.75 Kg, 0.82 mol, 1.26 equivalents), as a solution in DCM (0.23 L), was then added over 5 minutes, the cooling bath was removed and the obtained cloudy yellow solution was maintained at room temperature while stirring overnight, while monitoring the reaction completion by HPLC. Once the reaction was completed, the reaction mixture was cooled to 0±5° C. and stirred for at least 3 hours to precipitate DCU. The solids were then filtered and washed with DCM (1.2 L×2), the filtrates were combined and concentrated under reduced pressure (on a rotavap). The residue was then dissolved in EtOAc (5.8 L), transferred back to the 12 L round bottom flask using 1.1 L EtOAc to rinse the rotavap, and the obtained solution was cooled to 5±5° C., stirred for at least one hour and then filtered and washed with EtOAc (2×0.58 L). The filtrate was transferred to a separatory funnel and washed with 5% citric acid (1.2 L×2), 1M sodium bicarbonate (1.2 L×2) and brine (1.2 L×2). The organic layer was concentrated in vacuum and CAN (4.6 L) was added, followed by agitation at ≦50° C. until a homogeneous solution was obtained. The solution was transferred to 12 L 3-necked round bottom flask, equipped with mechanical stirrer, thermal well and nitrogen bubbler, using ACN (1.2 L). The solution was then cooled to 20±5° C., at which time solids began to form, and was stirred for 1 hour.

The solution was then cooled to 10±5° C. and stirred for 1.5±0.5 hours. The obtained solids were then filtered, washed with cold ACN (2×1.2 L) and air-dried for at least 30 minutes. The solids were then transferred to drying trays and dried at 35±5° C. under vacuum until constant weight, to give 1.62 Kg (98% yield) AN-197 as a yellow solid.

The purity of the compound was determined by the area percentage of HPLC as 99.1%.

The compound's structure was verified by $^1$H-NMR.

Karl Fischer (KF) titration analysis determined water content of 0.011%.

ROI was determined as 0.09%.

The amount of residual solvents was determined as meeting ICH guidelines for DCM, EtOAc and ACN:

DCM<165 ppm; EtOAc<162 ppm; ACN: 254 ppm.

In an additional exemplary batch, using the same general procedure as above, the following reagents were used:

| Reagents | MW | d (g/mL) | Equiv | mol | Weight (kg) | Volume (L) |
|---|---|---|---|---|---|---|
| Perphenazine | 403.97 | — | 1.0 | 1.76 | 0.710 | — |
| Boc-GABA | 203.24 | — | 1.2 | 2.11 | 0.429 | — |
| DCC | 206.33 | — | 1.28 | 2.22 | 0.458 | — |
| DMAP | 122.17 | — | 0.3 | 0.52 | 0.064 | — |
| DCM, anhy. | 84.93 | 1.33 | 7 vol | — | — | 4.91 |
| EtOAc | 88.11 | 0.90 | 7 vol | — | — | 5.1 |
| 5% citric acid | 192.12 | — | 2 vol | — | — | 1.4 |
| 1M sodium bicarbonate | 84.01 | — | 2 vol | — | — | 1.4 |
| brine | 58.44 | — | 2 vol | — | — | 1.4 |
| ACN | 41.05 | 0.79 | 7 vol | — | — | 4.9 | and the following product data were obtained:

| | 01BIL01-07 |
|---|---|
| Perphenazine Amount | 0.71 kg |
| AN-197 Lot Number | 01BIL01-07-78 |
| AN-197 Yield | 0.95 kg |
| Percent Yield | 91% |
| HPLC Purity | 99.9% |
| KF | 0.03% |
| ROI | 0.04% |
| Residual Solvents: | |
| ACN | <151 ppm |
| DCM | <150 ppm |
| EtOAc | <154 ppm |

In an additional batch (lot 01BIL01-02-64), 1.127 Kg perphenazine was converted to 1.75 Kg AN-197, using the same general procedure as above, with the following reagents:

| Reagents | MW | d (g/mL) | Equiv | mol | Weight (kg) | Volume (L) |
|---|---|---|---|---|---|---|
| Perphenazine | 403.97 | | 1.0 | 2.790 | 1.127 | |
| Boc-GABA | 203.24 | | 1.2 | 3.35 | 0.680 | |
| DCC | 206.33 | | 1.26 | 3.51 | 0.725 | |
| DMAP | 122.17 | | 0.3 | 0.835 | 0.102 | |
| DCM, anh. | | | 8 vol | | | 7.99 |
| EtOAc | | | 7 vol | | | 7.92 |
| 5% citric acid | | | 2 vol | | | 2.26 |
| 1M sodium bicarb | | | 2 vol | | | 2.26 |
| brine | | | 2 vol | | | 2.26 |
| ACN | | | 7 vol | | | 7.91 | and the following product data were obtained:

The purity of the compound was determined by the area percentage of HPLC as 98.4%.

The compound's structure was verified by $^1$H-NMR.

Karl Fischer (KF) titration analysis determined water content of 0.08%.

ROI was determined as 0.02%.

The amount of residual solvents was determined as meeting ICH guidelines for DCM, EtOAc and ACN:

DCM<106 ppm; EtOAc<99 ppm; ACN: 563 ppm.

Data relating to the preparation of additional batches of AN-197 are presented in U.S. Provisional Patent Application No. 61/307,482, filed Feb. 24, 2011, which is incorporated by reference as if fully set forth herein.

Preparation of a Trimesylate Salt of BL1020:

AN-197 was reacted with methanesulfonic acid (MSA), using a mixture of acetonitrile and butyl acetate, while performing in situ deprotection and salification (salt formation) of the N-protected chemical conjugate in a single-step synthesis, to thereby obtain the trimesylate salt of the perphenazine 4-aminobutyrate, using the following general procedure:

A three-necked round bottom flask, equipped with mechanical stirrer, addition funnel, thermal well and nitrogen inlet, is charged with AN-197 and butyl acetate (BAc), and the reaction mixture is stirred and heated to 40±5° C. During the heating period, ACN is added and most of the solids are dissolved. A solution of MSA and ACN is prepared and charged to the addition funnel and is added dropwise, at a rate to keep the internal temperature ≦40° C. The reaction is maintained at 40° C., and is monitored for completion by ion pair chromatography (IPC; AP-378), while determining completion at <1% AN-197. The solution is thereafter cooled to 15±5° C. and filtered through a B Buchner funnel. The solids are washed with cold (0±5° C.) mixture of 1:1 BAc/ACN and then with BAc. The resulting solids are dried under vacuum at 35±5° C. with a nitrogen purge for 90 hours with periodic crushing and turning of solids. The product is obtained as a white to pale pink solid.

In an exemplary procedure (Lot 06-01915-3), a 22 L three-necked round bottom flask, equipped with mechanical stirrer, addition funnel, thermal well and nitrogen inlet, was charged with AN-197 (0.832 Kg, 1.41 mol, 1.0 equivalent) and BAc (6.65 L), and the reaction mixture was stirred and heated to 40±5° C. During the heating period, ACN (6 L) was added and most of the solids were dissolved.

A solution of MSA (0.385 L, 5.93 mol, 4.2 equivalents) and ACN (0.5 L) was prepared and charged to the addition funnel and was added dropwise, at a rate to keep the internal temperature ≦40° C. The reaction was maintained at 40° C., and was monitored for completion by ion chromatography (IPC; AP-378), while determining completion at <1% AN-197 after 24 hours. The solution was thereafter cooled to 15±5° C. and filtered through a B Buchner funnel. The solids were washed with cold (0±5° C.) mixture of 1:1 BAc/ACN (2×1.7 L) and then with BAc (2×1.7 L). The resulting solids were dried under vacuum at 35±5° C. with a nitrogen purge for 90 hours with periodic crushing and turning of solids. The product was obtained as a white solid (1.045 Kg; 95% yield).

HPLC analysis of the product determined a purity of 99.4, by area percentages (AP), the presence of 0.20 AP perphenazine, 0.40 AP AN-197, and less than 0.50 AP other impurities.

$^1$H-NMR, $^{13}$C-NMR and IR spectra were consistent with the product's structure.

Karl Fischer (KF) titration analysis determined water content of 0.5%.

ROI was determined as 0.23%.

DSC showed an endothermic peak at 214.8° C. (see, FIG. 1).

Ion Chromatography determined MSA 38.4 ppm and Cl 0.074 ppm.

Amount of residual solvents was determined as DCM<124 ppm; EtOAc<87 ppm; CAN<410 ppm; and BAc<96 ppm.

Heavy metals content was less than 0.0002%.

Ion content was determined as MSA 38.4% and Cl 741 ppm

| Elemental Analysis: | Theory | Found |
|---|---|---|
| C | 43.26 | 43.47 |
| H | 5.83 | 5.74 |
| N | 7.21 | 7.19 |
| Cl | 4.56 | 4.53 |
| S | 16.50 | 16.58 |

In an additional exemplary batch (Lot 01BIL02-03-22), the following reagents were used for converting AN-197 to BL1020 MSA salt using the procedure described hereinabove:

| Reagents | MW | d (g/mL) | Equiv | mol | Weight (kg) | Volume (L) |
|---|---|---|---|---|---|---|
| AN-197 | 589.19 | — | 1.0 | 2.63 | 1.55 | — |
| MSA (methanesulfonic acid) | 96.11 | 1.481 | 4.2 | 11 | — | 0.73 |
| BAc (butyl acetate) | | | 10 vol | | | 18.6 |
| ACN (acetonitrile) | | | 8 vol | | | 12.4 |
| 1:1/BAc:ACN | | | 4 vol | | | 6.2 |

A 50 L three-necked round bottom flask was used, and the reaction mixture was heated at 40±2° C. for 19 hours, upon determining completion. After filtering and washing the obtained solids, drying was effected with a nitrogen purge as described hereinabove until constant weight. Residual solvents were monitored by drying IPC—material was deemed dry when ICH guidelines for ACN, BAc, DCM and EtOAc were met. The product was obtained as a white solid (1.95 Kg; 95.1% yield).

IR and NMR spectra were consistent with the product's structure.

HPLC analysis of the product determined a purity of 99.2, by area percentages (AP), the presence of 0.12 AP perphenazine, 0.41 AP AN-197, 0.09 AP Bis(GABA)-BL1020, and less than 0.15 AP other impurities.

Karl Fischer (KF) titration analysis determined water content of 0.36%.

ROI was determined as 0.07%.

Amount of residual solvents was determined as DCM<158 ppm; EtOAc<149 ppm; ACN<153 ppm; and BAc: 333 ppm.

In an additional exemplary batch (Lot 01BIL02-07-34), 0.95 Kg AN-197 was converted to 1.25 Kg BL1020 MSA salt using the procedure described hereinabove and the following reagents:

| Reagents | MW | d (g/mL) | Equiv | mol | Weight (kg) | Volume (L) |
|---|---|---|---|---|---|---|
| AN-197 | 589.19 | — | 1.0 | 1.6 | 0.95 | — |
| MSA (methanesulfonic acid) | 96.11 | 1.481 | 4.3 | 6.8 | — | 0.44 |
| BAc (butyl acetate) | 116.16 | 0.88 | 12 vol | | | 11.4 |
| ACN (acetonitrile) | 41.05 | 0.79 | 8 vol | | | 7.6 |
| 1:1/BAc:ACN | — | — | 4 vol | — | — | 3.8 |

A 50 L three-necked round bottom flask was used, and the reaction mixture was heated at 40±2° C. for 16 hours, upon determining completion. After filtering and washing the obtained solids, drying was effected with a nitrogen purge as described hereinabove until constant weight. Residual solvents were monitored by drying IPC—material was deemed dry when ICH guidelines for ACN, BAc, DCM and EtOAc were met. The product was obtained as a white solid (1.25 Kg; 100% yield).

IR and NMR spectra were consistent with the product's structure.

HPLC analysis of the product determined a purity of 99.3, by area percentages (AP), the presence of 0.11 AP perphenazine, and 0.22 AP AN-197, 0.11 AP Bis(GABA)-BL1020, and less than 0.10 AP other impurities.

DSC showed an endothermic peak at 212.6° C.

Karl Fischer (KF) titration analysis determined water content of 0.36%.

ROI was determined as 0.01%.

Amount of residual solvents was determined as DCM<153 ppm; EtOAc<156 ppm; ACN<151 ppm; and BAc: 200 ppm.

Ion Chromatography determined MSA 37.3 ppm and Cl 120 ppm.

In an additional exemplary batch (Lot 01BIL02-02-22), 1.70 Kg AN-197 was converted to 2.10 Kg BL1020 MSA salt using the procedure described hereinabove and the following reagents:

| Reagents | MW | d (g/mL) | Equiv | mol | Weight (kg) | Volume (L) |
|---|---|---|---|---|---|---|
| AN-197 | 589.19 | | 1.0 | 2.89 | 1.70 | |
| MSA (methanesulfonic acid) | 96.11 | 1.481 | 4.2 | 12.2 | | 0.79 |
| BAc (butyl acetate) | | | 10 vol | | | 20.4 |
| ACN (acetonitrile) | | | 8 vol | | | 13.6 |
| 1:1/BAc:ACN | | | 4 vol | | | 6.8 |

A 50 L three-necked round bottom flask was used, and the reaction mixture was heated at 40±2° C. for 16 hours, upon determining completion. After filtering and washing the obtained solids, drying was effected with a nitrogen purge as described hereinabove until constant weight. Residual solvents were monitored by drying IPC—material was deemed dry when ICH guidelines for ACN, BAc, DCM and EtOAc were met. The product was obtained as a white solid (2.10 Kg; 93.8% yield).

IR and NMR spectra were consistent with the product's structure.

HPLC analysis of the product determined a purity of 99.3, by area percentages (AP), the presence of 0.13 AP perphenazine, 0.37 AP AN-197, 0.06 AP Bis(GABA)-BL1020, and less than 0.15 AP other impurities.

Karl Fischer (KF) titration analysis determined water content of 0.44%.

ROI was determined as 0.03%.

Amount of residual solvents was determined as DCM<153 ppm; EtOAc<151 ppm; ACN<154 ppm; and BAc: 353 ppm.

Data relating to the preparation of additional batches of BL1020 MSA salts are presented in U.S. Provisional Patent Application Nos. 61/307,481 and 61/307,482, co-filed Feb. 24, 2010, which are incorporated by reference as if fully set forth herein.

Example 3

Characterization of a Crystalline Form of the Trimesylate Salt of perphenazine-γ-butyrate Several lots of BL-1020 MSA salts prepared as described in Example 2 hereinabove were further subjected to X-Ray powder diffraction (XRPD), moisture absorption/desorption (DVS), light microscopy, BET surface area, Malvern particle size and bulk and tapped density analyses.

Brief Summary of Results

XRPD patterns suggest that all tested lots of BL-1020 MSA salt contain the same crystalline form;

DVS data indicate that the samples have about 5% water retention;

Light microscopy evaluations, surface area, density testing and particle size analyses demonstrated that similar values were obtained for most of the tested lots: The material consisted of needles and spherulite fragments exhibiting birefringence with extinction; Surface area ranged from 4.57 to 4.93 $m^2/g$; the bulk and tapped density results ranged from 0.13 to 0.18 g/ml (bulk) and from 0.22 to 0.26 g/ml (tapped); and particles showed predominantly unimodal distributions with a tail of fines below 1 μm, and particle sizes up to approximately 100 μm.

It is noted that for some of the tested lots, the obtained data was outside one or more of the above-indicated values, presumably due to formation of aggregates.

Instrumental Data

XRPD:

XRPD patterns were collected using a PANalytical XPert Pro diffractor. The specimen was analyzed using Cu Kα radiation produced using an Optix ling fine-focus source. An elliptically graded multilayerd mirror was used to focus Cu Kα X-rays of the source through the specimen and onto the detector. The specimen was sandwiched between 3 microns thick films, analyzed in transmission geometry, and rotated to optimize orientation statistics. A beam-stop was used to minimize the background generated by air scattering. Helium and the anti-scatter extension were not used. Soller slits were used for the incident and diffracted beams to minimize axial divergence. Diffraction patterns were collected using a scanning position-sensitive detector (XCelerator) located 240 mm from the specimen. Prior to the analysis, a silicon specimen (NIST standard reference material 640c) was analyzed to verify the position of the silicon 111 peak.

DVS:

Moisture absorption/desorption (DVS) data was collected on a VTI SGA-100 Vapor Sorption Analyzer. Absorption and desorption data were collected over a range of 5% to 95% relative humidity (RH) at 10% RH intervals under a nitrogen purge. Samples were not dried prior to analyses. Equilibrium criteria used for analyses were less than 0.0100% weight change in 5 minutes, with a maximum equilibrium time of 3 hours if the weight criterion was not met. Data were not corrected for the initial moisture content of the samples. NaCl and PVP were used as calibration standards.

Polarized Light Microscopy:

Polarized light microscopy was performed using a Leica DM LP microscope equipped with Spot Insight color camera (model 3.2.0). A 20× or 40× objective was used with the cross polarizers and a first order red compensator in place to view the sample. Samples were placed on a glass slide, then a cover glass was placed over the sample, and a drop of mineral oil was added. Additionally, a sample pre-dispersed in 0.1% (w/v) SPAN 85 in hexane was placed on a glass slide and covered with a cover glass. Images were acquired at ambient temperature using Spot software (v.4.5.9 for Windows). Micron bars were inserted onto the images as a reference for particle size.

BET Surface Area:

Surface area data were collected using nitrogen absorption on a BET Micrometics Gemini V (11-point BET analysis) analyzer. The samples were outgassed at 40° C. under vacuum for at least 2 hours. SRM 1899 and SRM 1900 were used as the calibration standards.

Refractive Index Determination:

Refractive index determination was performed using a Leica DM LP microscope. A single, sub-stage polarizer was used to view samples. Samples were placed on a glass slide, a coverslip was placed over the sample, and a drop of a certified Cargille refractive index oil was added. The movement of the Becke line was observed while defocusing the sample.

Particle Size:

Particle size data was acquired using a Malvern Instruments MS2000 equipped with a Hydro2000 μP dispersion unit. Data was collected and analyzed with Mastersizer 2000 v. 5.1 software, using volume based measurements. NIST traceable glass beads were used as the reference standard.

The final method conditions selected for determining the particle size of BL-1020 MSA salts were as follows:

Sample refractive index: 1.56;
Sample absorption: 0.1;
Dispersant: ~1% (w/v) SPAN 85 in hexane;
Dispersant refractive index: 1.39;
Pump speed: 1000 rpm;
Recirculation time: 10 seconds;
Sample measurement time: 10 seconds;
Background measurement time: 10 seconds;
Sonication: 10 seconds (100% power);
Model: general purpose;
Sensitivity: normal.

Bulk and Tapped Density:

Samples were submitted to Particle Technology Labs (PTL), Downers Grove, Ill., for bulk and tapped density analyses.

Results

XRPD:

As shown in FIGS. 2 and 3A-I, the XRPD patterns of all tested lots of BL-1020 MSA salt, referred to herein as lots 06-01915-3; 01BIL02-01-22; 01BIL02-02-22; 01BIL02-03-22; 01BIL02-04-22; 01BIL02-05-26, 01CYS02-01-37, 01BIL02-07-34, and 01BIL02-06-26 display resolution of reflections which indicate that these lots contain a crystalline material. The patterns are all similar to one another in terms of peak positions and relative peak intensities, indicating that the samples are the same crystalline form.

Figure 3A:
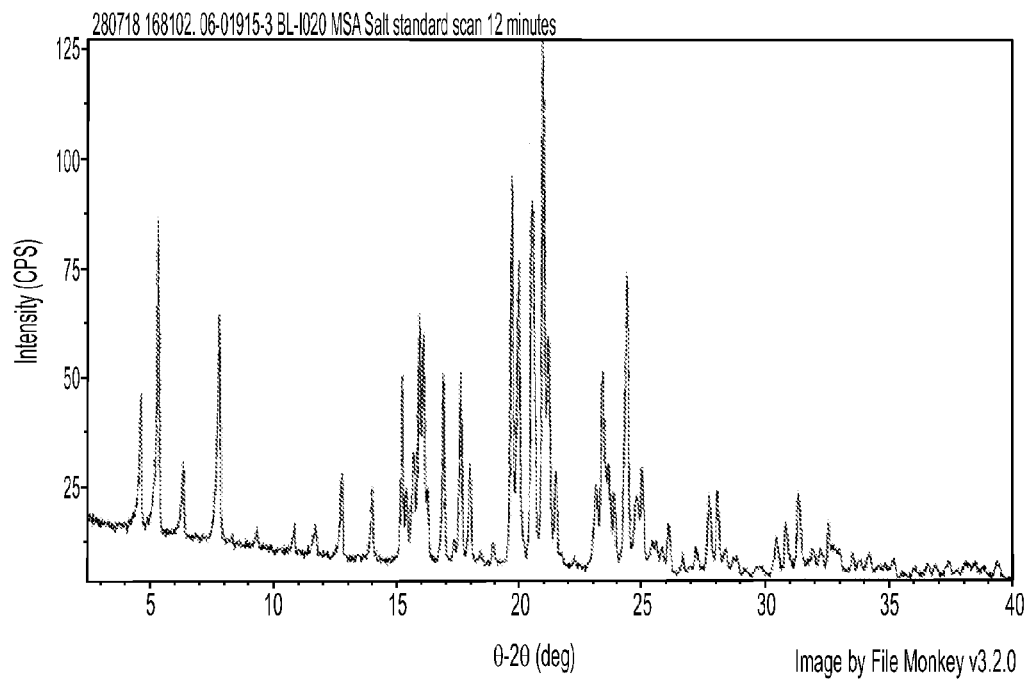
FIGS. 3A-I present XRPD patterns obtained for exemplary lots of BL-2010 MSA salt (Lot 06-01915-3 in FIG. 3A; Lot 01BIL02-01-22 in FIG. 3B; Lot 01BIL02-02-22 in FIG. 3C; Lot 01BIL02-03-22 in FIG. 3D; Lot 01BIL02-04-22 in FIG. 3E; Lot 01BIL02-05-26 in FIG. 3F; Lot 01CYS02-01-37 IN FIG. 3G; Lot 01BIL02-07-34 in FIG. 3H; and Lot 01BIL02-06-26 in FIG. 3I)
Figure 3B:
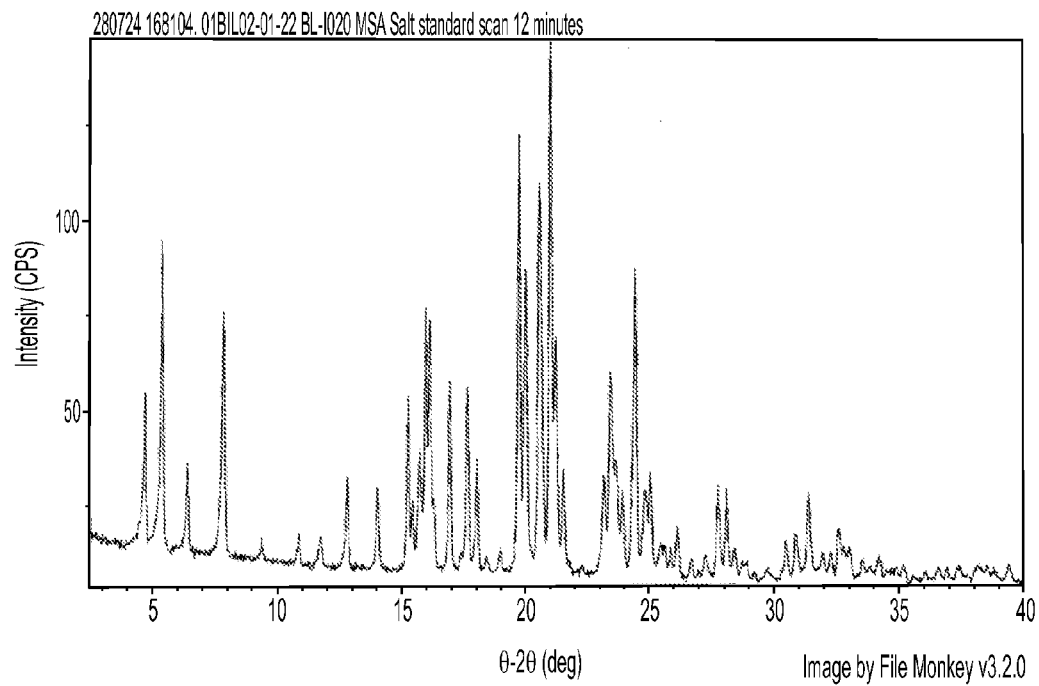
Figure 3C:
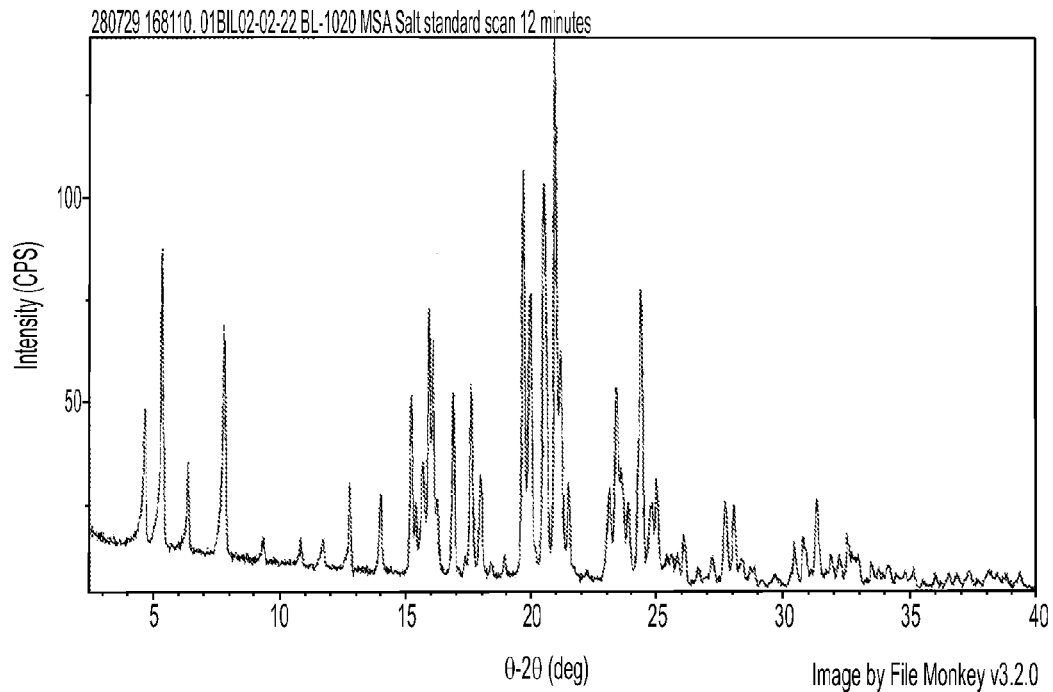
Figure 3D:
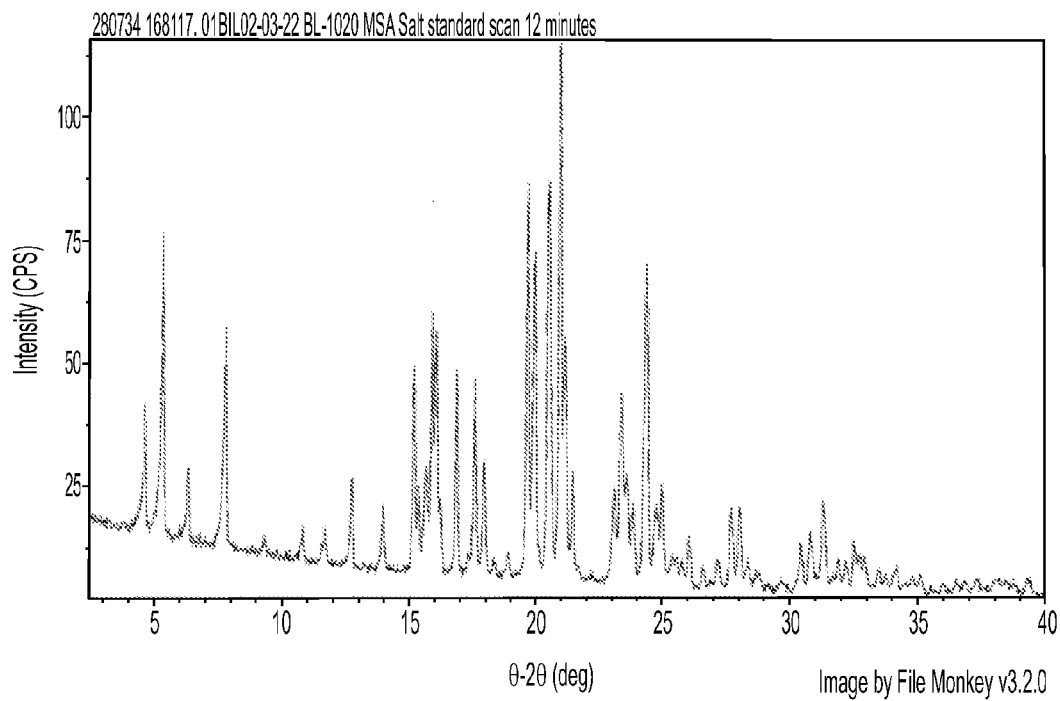
Figure 3E:
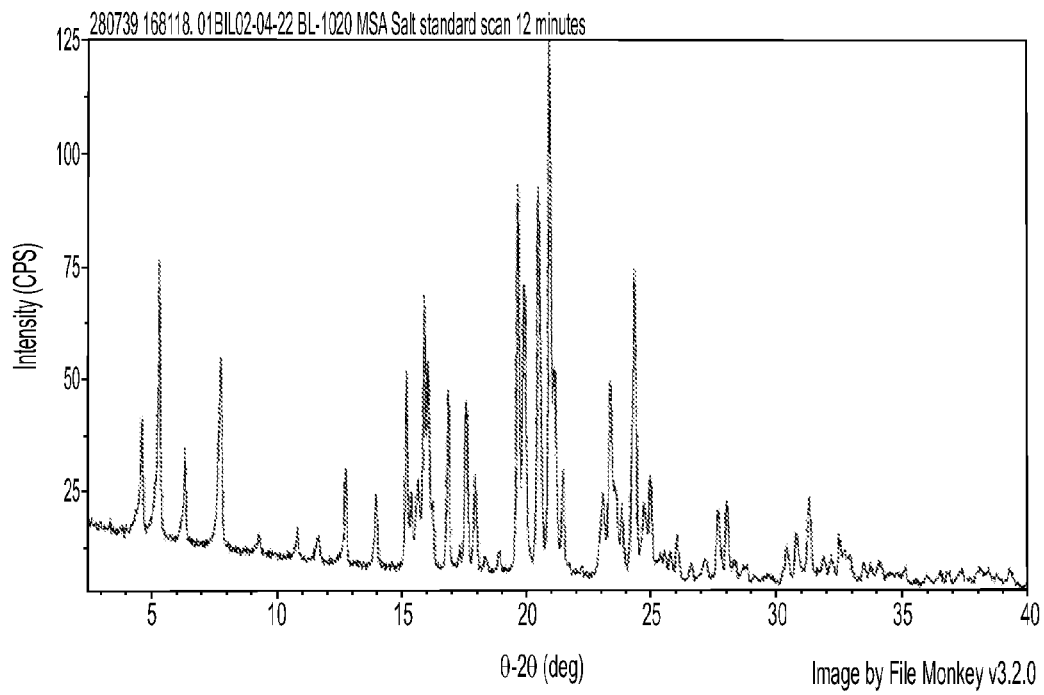
Figure 3F:
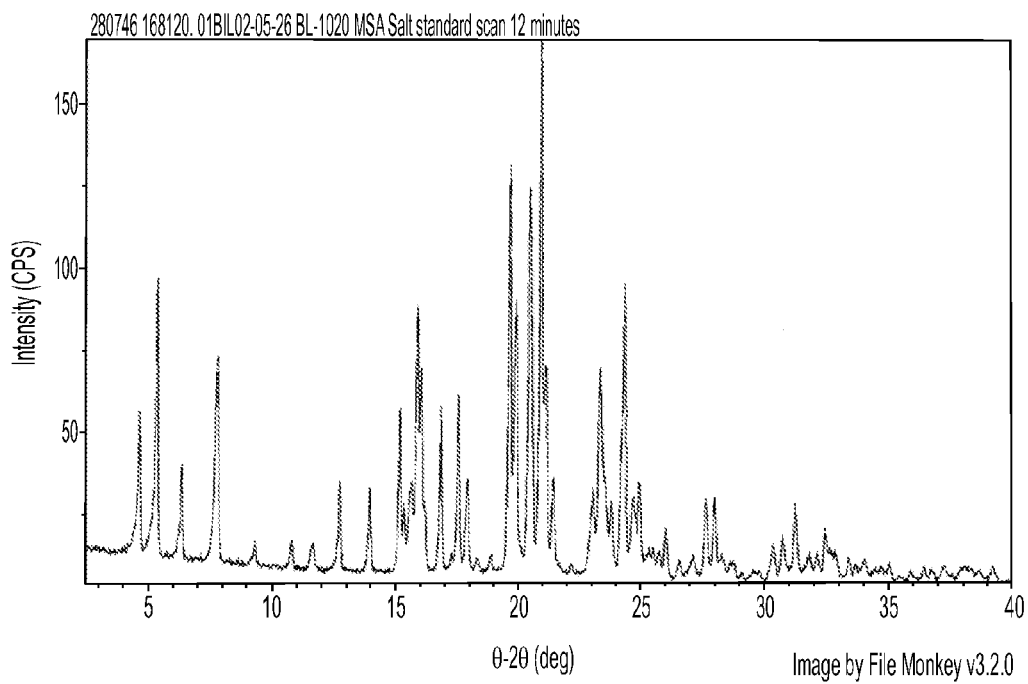
Figure 3G:
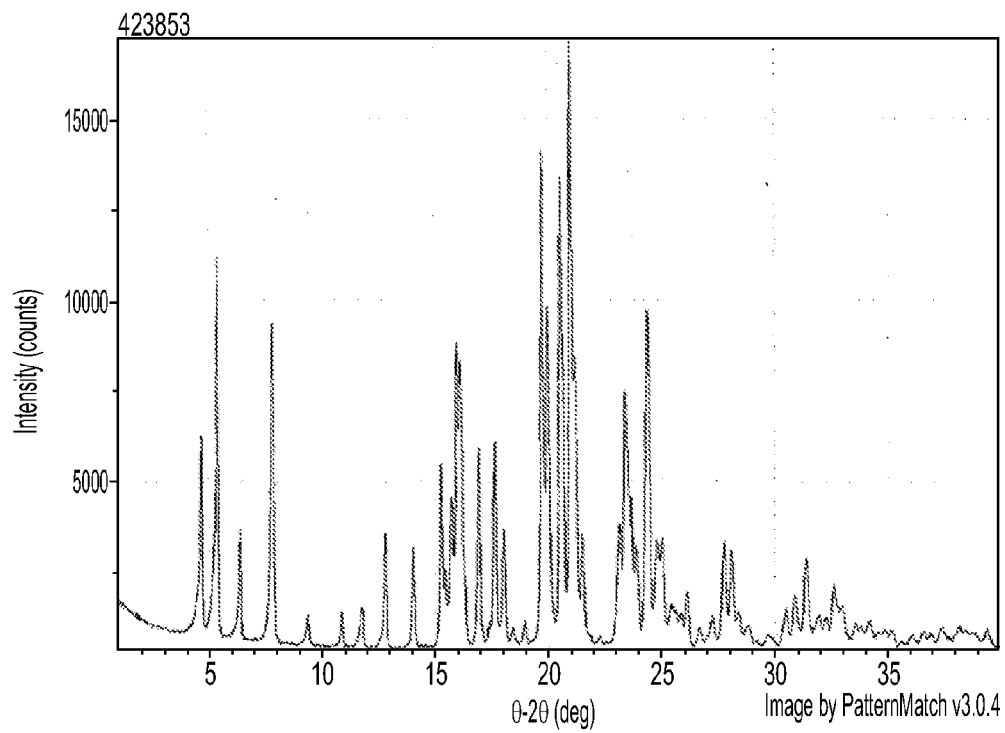
Figure 3H:
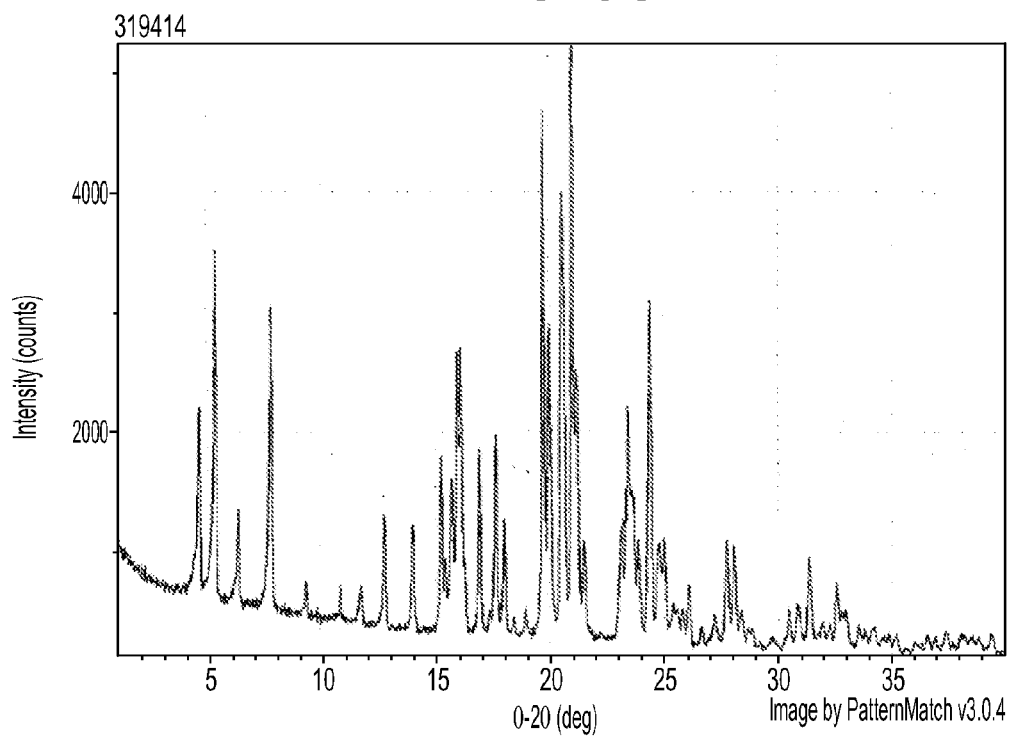
Figure 3I:
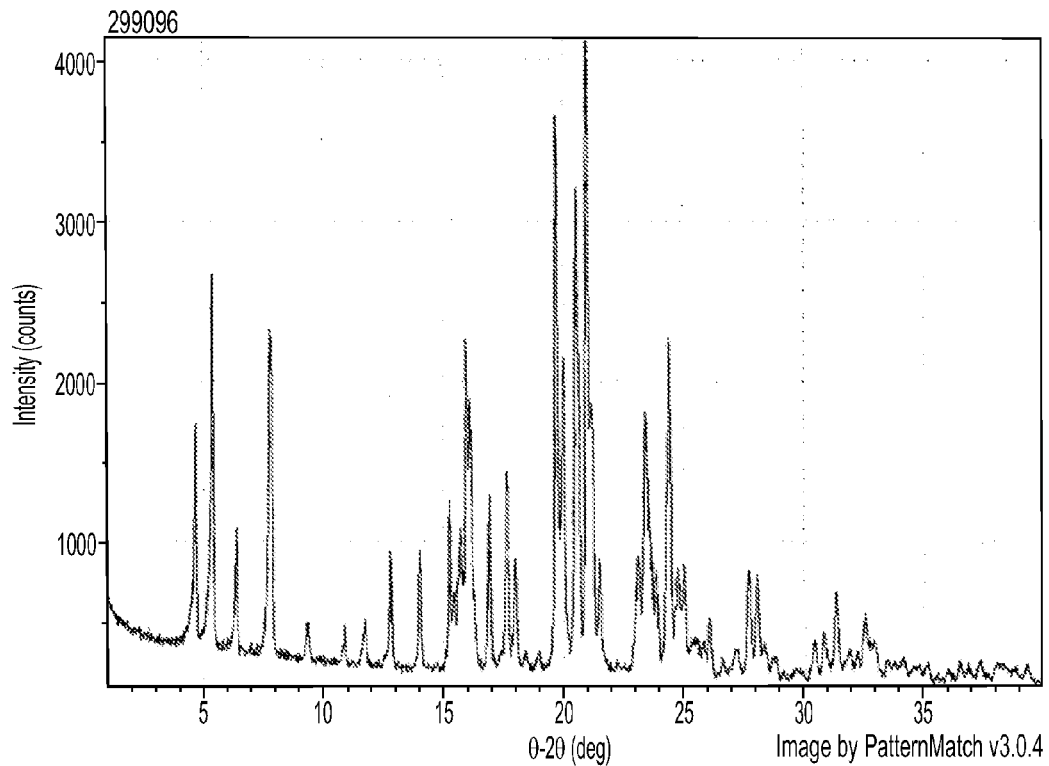

Representative XRPD patterns (for lot 06-01915-3) are presented in FIGS. 3A-F, for lots 06-01915-3; 01BIL02-01-22; 01BIL02-02-22; 01BIL02-03-22; 01BIL02-04-22; and 01BIL02-05-26, respectively, and XRPD patterns for lots 01CYS02-01-37, 01BIL02-07-34, and 01BIL02-06-26 are presented in FIGS. 3G-I.

Tables of observed and prominent peaks observed in various XRPD patterns are presented below:

TABLE 1

Observed peaks for CYP-1020 (BL-1020) MSA salt, lot 01CYS02-01-37, XRPD file 423853

| 2Θ (°) | d space (Å) | Intensity (%) |
|---|---|---|
| 4.66 ± 0.20 | 18.946 ± 0.848 | 36 |
| 5.38 ± 0.20 | 16.418 ± 0.633 | 65 |
| 6.39 ± 0.20 | 13.842 ± 0.447 | 22 |
| 7.82 ± 0.20 | 11.302 ± 0.296 | 55 |
| 9.36 ± 0.20 | 9.449 ± 0.206 | 8 |
| 10.85 ± 0.20 | 8.156 ± 0.153 | 8 |
| 11.73 ± 0.20 | 7.543 ± 0.130 | 9 |
| 12.79 ± 0.20 | 6.924 ± 0.110 | 21 |
| 14.02 ± 0.20 | 6.316 ± 0.091 | 18 |
| 15.26 ± 0.20 | 5.807 ± 0.077 | 32 |
| 15.43 ± 0.20 | 5.744 ± 0.075 | 15 |
| 15.71 ± 0.20 | 5.641 ± 0.072 | 26 |
| 15.96 ± 0.20 | 5.553 ± 0.070 | 51 |
| 16.11 ± 0.20 | 5.501 ± 0.069 | 48 |
| 16.93 ± 0.20 | 5.237 ± 0.062 | 34 |
| 17.38 ± 0.20 | 5.102 ± 0.059 | 7 |
| 17.65 ± 0.20 | 5.025 ± 0.057 | 35 |
| 18.02 ± 0.20 | 4.924 ± 0.055 | 21 |
| 18.43 ± 0.20 | 4.813 ± 0.052 | 6 |
| 18.95 ± 0.20 | 4.683 ± 0.049 | 7 |
| 19.72 ± 0.20 | 4.502 ± 0.046 | 81 |
| 19.99 ± 0.20 | 4.442 ± 0.044 | 57 |
| 20.56 ± 0.20 | 4.321 ± 0.042 | 77 |
| 21.01 ± 0.20 | 4.229 ± 0.040 | 100 |
| 21.19 ± 0.20 | 4.193 ± 0.039 | 49 |
| 21.51 ± 0.20 | 4.131 ± 0.038 | 20 |
| 22.26 ± 0.20 | 3.994 ± 0.036 | 4 |
| 23.13 ± 0.20 | 3.845 ± 0.033 | 22 |
| 23.41 ± 0.20 | 3.799 ± 0.032 | 43 |
| 23.61 ± 0.20 | 3.768 ± 0.032 | 27 |
| 23.88 ± 0.20 | 3.726 ± 0.031 | 19 |
| 24.38 ± 0.20 | 3.651 ± 0.030 | 56 |
| 24.78 ± 0.20 | 3.592 ± 0.029 | 20 |
| 25.02 ± 0.20 | 3.559 ± 0.028 | 20 |

TABLE 2

Prominent peaks for CYP-1020 (BL-1020) MSA salt, lot 01CYS02-01-37, XRPD file 423853

| 2Θ (°) | d space (Å) | Intensity (%) |
|---|---|---|
| 4.66 ± 0.20 | 18.946 ± 0.848 | 36 |
| 5.38 ± 0.20 | 16.418 ± 0.633 | 65 |
| 6.39 ± 0.20 | 13.842 ± 0.447 | 22 |
| 7.82 ± 0.20 | 11.302 ± 0.296 | 55 |
| 12.79 ± 0.20 | 6.924 ± 0.110 | 21 |
| 14.02 ± 0.20 | 6.316 ± 0.091 | 18 |
| 15.26 ± 0.20 | 5.807 ± 0.077 | 32 |
| 15.71 ± 0.20 | 5.641 ± 0.072 | 26 |
| 15.96 ± 0.20 | 5.553 ± 0.070 | 51 |
| 16.11 ± 0.20 | 5.501 ± 0.069 | 48 |
| 16.93 ± 0.20 | 5.237 ± 0.062 | 34 |
| 17.65 ± 0.20 | 5.025 ± 0.057 | 35 |
| 18.02 ± 0.20 | 4.924 ± 0.055 | 21 |
| 19.72 ± 0.20 | 4.502 ± 0.046 | 81 |
| 19.99 ± 0.20 | 4.442 ± 0.044 | 57 |
| 20.56 ± 0.20 | 4.321 ± 0.042 | 77 |
| 21.01 ± 0.20 | 4.229 ± 0.040 | 100 |
| 21.19 ± 0.20 | 4.193 ± 0.039 | 49 |

TABLE 3

Observed peaks for CYP-1020 (BL-1020) MSA salt, lot 01BIL02-07-34, XRPD file 319414

| 2Θ (°) | d space (Å) | Intensity (%) |
|---|---|---|
| 4.67 ± 0.20 | 18.930 ± 0.847 | 42 |
| 5.39 ± 0.20 | 16.406 ± 0.632 | 67 |
| 6.39 ± 0.20 | 13.834 ± 0.447 | 26 |
| 7.83 ± 0.20 | 11.296 ± 0.296 | 58 |
| 9.35 ± 0.20 | 9.462 ± 0.206 | 14 |
| 10.87 ± 0.20 | 8.141 ± 0.152 | 14 |
| 11.74 ± 0.20 | 7.540 ± 0.130 | 14 |
| 12.79 ± 0.20 | 6.922 ± 0.110 | 25 |
| 14.01 ± 0.20 | 6.322 ± 0.091 | 23 |
| 15.26 ± 0.20 | 5.805 ± 0.077 | 34 |
| 15.43 ± 0.20 | 5.743 ± 0.075 | 18 |
| 15.71 ± 0.20 | 5.639 ± 0.072 | 31 |
| 15.95 ± 0.20 | 5.557 ± 0.070 | 51 |
| 16.12 ± 0.20 | 5.500 ± 0.069 | 51 |
| 16.28 ± 0.20 | 5.444 ± 0.067 | 18 |
| 16.93 ± 0.20 | 5.236 ± 0.062 | 35 |
| 17.39 ± 0.20 | 5.101 ± 0.059 | 10 |
| 17.65 ± 0.20 | 5.024 ± 0.057 | 37 |
| 18.02 ± 0.20 | 4.923 ± 0.055 | 24 |
| 18.42 ± 0.20 | 4.816 ± 0.052 | 9 |
| 18.96 ± 0.20 | 4.682 ± 0.049 | 10 |
| 19.72 ± 0.20 | 4.501 ± 0.046 | 85 |
| 20.01 ± 0.20 | 4.438 ± 0.044 | 55 |
| 20.56 ± 0.20 | 4.320 ± 0.042 | 76 |
| 21.00 ± 0.20 | 4.231 ± 0.040 | 100 |
| 21.18 ± 0.20 | 4.195 ± 0.040 | 48 |
| 21.51 ± 0.20 | 4.131 ± 0.038 | 20 |
| 23.12 ± 0.20 | 3.848 ± 0.033 | 23 |
| 23.40 ± 0.20 | 3.801 ± 0.032 | 42 |
| 23.60 ± 0.20 | 3.770 ± 0.032 | 27 |
| 23.89 ± 0.20 | 3.725 ± 0.031 | 21 |
| 24.40 ± 0.20 | 3.648 ± 0.030 | 59 |
| 24.79 ± 0.20 | 3.592 ± 0.029 | 20 |
| 25.01 ± 0.20 | 3.561 ± 0.028 | 21 |

TABLE 4

Prominent peaks for CYP-1020 (BL-1020) MSA salt, lot 01BIL02-07-34, XRPD file 319414

| 2Θ (°) | d space (Å) | Intensity (%) |
|---|---|---|
| 4.67 ± 0.20 | 18.930 ± 0.847 | 42 |
| 5.39 ± 0.20 | 16.406 ± 0.632 | 67 |
| 6.39 ± 0.20 | 13.834 ± 0.447 | 26 |
| 7.83 ± 0.20 | 11.296 ± 0.296 | 58 |
| 12.79 ± 0.20 | 6.922 ± 0.110 | 25 |
| 14.01 ± 0.20 | 6.322 ± 0.091 | 23 |
| 15.26 ± 0.20 | 5.805 ± 0.077 | 34 |
| 15.71 ± 0.20 | 5.639 ± 0.072 | 31 |
| 15.95 ± 0.20 | 5.557 ± 0.070 | 51 |
| 16.12 ± 0.20 | 5.500 ± 0.069 | 51 |
| 16.93 ± 0.20 | 5.236 ± 0.062 | 35 |
| 17.65 ± 0.20 | 5.024 ± 0.057 | 37 |
| 18.02 ± 0.20 | 4.923 ± 0.055 | 24 |
| 19.72 ± 0.20 | 4.501 ± 0.046 | 85 |
| 20.01 ± 0.20 | 4.438 ± 0.044 | 55 |
| 20.56 ± 0.20 | 4.320 ± 0.042 | 76 |
| 21.00 ± 0.20 | 4.231 ± 0.040 | 100 |
| 21.18 ± 0.20 | 4.195 ± 0.040 | 48 |

TABLE 5

Observed peaks for CYP-1020 (BL-1020) MSA salt, lot 01BIL02-06-26, XRPD file 299096

| 2Θ (°) | d space (Å) | Intensity (%) |
|---|---|---|
| 4.67 ± 0.20 | 18.930 ± 0.847 | 42 |
| 5.37 ± 0.20 | 16.457 ± 0.636 | 63 |

TABLE 5-continued

Observed peaks for CYP-1020 (BL-1020) MSA salt, lot 01BIL02-06-26, XRPD file 299096

| 2Θ (°) | d space (Å) | Intensity (%) |
|---|---|---|
| 6.39 ± 0.20 | 13.834 ± 0.447 | 26 |
| 7.81 ± 0.20 | 11.320 ± 0.297 | 56 |
| 9.33 ± 0.20 | 9.479 ± 0.207 | 12 |
| 10.85 ± 0.20 | 8.153 ± 0.153 | 12 |
| 11.70 ± 0.20 | 7.562 ± 0.131 | 11 |
| 12.79 ± 0.20 | 6.922 ± 0.110 | 23 |
| 14.01 ± 0.20 | 6.322 ± 0.091 | 23 |
| 15.25 ± 0.20 | 5.811 ± 0.077 | 30 |
| 15.43 ± 0.20 | 5.743 ± 0.075 | 16 |
| 15.70 ± 0.20 | 5.645 ± 0.072 | 26 |
| 15.95 ± 0.20 | 5.557 ± 0.070 | 54 |
| 16.10 ± 0.20 | 5.506 ± 0.069 | 44 |
| 16.25 ± 0.20 | 5.455 ± 0.068 | 17 |
| 16.90 ± 0.20 | 5.246 ± 0.062 | 32 |
| 17.64 ± 0.20 | 5.029 ± 0.057 | 34 |
| 17.99 ± 0.20 | 4.932 ± 0.055 | 21 |
| 18.40 ± 0.20 | 4.821 ± 0.053 | 7 |
| 18.96 ± 0.20 | 4.682 ± 0.049 | 7 |
| 19.71 ± 0.20 | 4.505 ± 0.046 | 88 |
| 19.98 ± 0.20 | 4.445 ± 0.045 | 52 |
| 20.54 ± 0.20 | 4.323 ± 0.042 | 77 |
| 21.00 ± 0.20 | 4.231 ± 0.040 | 100 |
| 21.18 ± 0.20 | 4.195 ± 0.040 | 45 |
| 21.50 ± 0.20 | 4.134 ± 0.038 | 21 |
| 23.10 ± 0.20 | 3.850 ± 0.033 | 20 |
| 23.40 ± 0.20 | 3.801 ± 0.032 | 44 |
| 23.62 ± 0.20 | 3.767 ± 0.032 | 26 |
| 23.87 ± 0.20 | 3.728 ± 0.031 | 20 |
| 24.39 ± 0.20 | 3.650 ± 0.030 | 55 |
| 24.77 ± 0.20 | 3.594 ± 0.029 | 21 |
| 25.01 ± 0.20 | 3.561 ± 0.028 | 21 |

TABLE 6

Prominent peaks for CYP-1020 (BL-1020) MSA salt, lot 01BIL02-07-34, XRPD file 319414

| 2Θ (°) | d space (Å) | Intensity (%) |
|---|---|---|
| 4.67 ± 0.20 | 18.930 ± 0.847 | 42 |
| 5.37 ± 0.20 | 16.457 ± 0.636 | 63 |
| 6.39 ± 0.20 | 13.834 ± 0.447 | 26 |
| 7.81 ± 0.20 | 11.320 ± 0.297 | 56 |
| 12.79 ± 0.20 | 6.922 ± 0.110 | 23 |
| 14.01 ± 0.20 | 6.322 ± 0.091 | 23 |
| 15.25 ± 0.20 | 5.811 ± 0.077 | 30 |
| 15.70 ± 0.20 | 5.645 ± 0.072 | 26 |
| 15.95 ± 0.20 | 5.557 ± 0.070 | 54 |
| 16.10 ± 0.20 | 5.506 ± 0.069 | 44 |
| 16.90 ± 0.20 | 5.246 ± 0.062 | 32 |
| 17.64 ± 0.20 | 5.029 ± 0.057 | 34 |
| 17.99 ± 0.20 | 4.932 ± 0.055 | 21 |
| 19.71 ± 0.20 | 4.505 ± 0.046 | 88 |
| 19.98 ± 0.20 | 4.445 ± 0.045 | 52 |
| 20.54 ± 0.20 | 4.323 ± 0.042 | 77 |
| 21.00 ± 0.20 | 4.231 ± 0.040 | 100 |
| 21.18 ± 0.20 | 4.195 ± 0.040 | 45 |

TABLE 7

Observed peaks for CYP-1020 (BL-1020) MSA salt, lot 01BIL02-01-22, XRPD file 280724

| 2Θ (°) | d space (Å) | Intensity (%) |
|---|---|---|
| 4.68 ± 0.20 | 18.862 ± 0.841 | 37 |
| 5.39 ± 0.20 | 16.406 ± 0.632 | 64 |
| 6.39 ± 0.20 | 13.834 ± 0.447 | 25 |
| 7.84 ± 0.20 | 11.272 ± 0.295 | 51 |
| 9.38 ± 0.20 | 9.428 ± 0.205 | 11 |
| 10.87 ± 0.20 | 8.141 ± 0.152 | 12 |
| 11.75 ± 0.20 | 7.529 ± 0.130 | 11 |
| 12.79 ± 0.20 | 6.922 ± 0.110 | 22 |
| 14.03 ± 0.20 | 6.314 ± 0.091 | 20 |
| 15.26 ± 0.20 | 5.805 ± 0.077 | 36 |
| 15.43 ± 0.20 | 5.743 ± 0.075 | 18 |
| 15.73 ± 0.20 | 5.634 ± 0.072 | 27 |
| 15.96 ± 0.20 | 5.551 ± 0.070 | 52 |
| 16.13 ± 0.20 | 5.494 ± 0.069 | 50 |
| 16.28 ± 0.20 | 5.444 ± 0.067 | 18 |
| 16.93 ± 0.20 | 5.236 ± 0.062 | 39 |
| 17.39 ± 0.20 | 5.101 ± 0.059 | 9 |
| 17.65 ± 0.20 | 5.024 ± 0.057 | 38 |
| 18.04 ± 0.20 | 4.918 ± 0.055 | 25 |
| 18.42 ± 0.20 | 4.816 ± 0.052 | 8 |
| 18.97 ± 0.20 | 4.678 ± 0.049 | 9 |
| 19.72 ± 0.20 | 4.501 ± 0.046 | 83 |
| 20.01 ± 0.20 | 4.438 ± 0.044 | 58 |
| 20.56 ± 0.20 | 4.320 ± 0.042 | 74 |
| 21.00 ± 0.20 | 4.231 ± 0.040 | 100 |
| 21.21 ± 0.20 | 4.189 ± 0.039 | 47 |
| 21.51 ± 0.20 | 4.131 ± 0.038 | 23 |
| 22.28 ± 0.20 | 3.990 ± 0.036 | 6 |
| 23.15 ± 0.20 | 3.842 ± 0.033 | 22 |
| 23.42 ± 0.20 | 3.799 ± 0.032 | 39 |
| 23.64 ± 0.20 | 3.764 ± 0.032 | 24 |
| 23.89 ± 0.20 | 3.725 ± 0.031 | 19 |
| 24.40 ± 0.20 | 3.648 ± 0.030 | 59 |
| 24.81 ± 0.20 | 3.589 ± 0.029 | 18 |
| 25.02 ± 0.20 | 3.559 ± 0.028 | 23 |

TABLE 8

Prominent peaks for CYP-1020 (BL-1020) MSA salt, lot 01BIL02-01-22, XRPD file 280724

| 2Θ (°) | d space (Å) | Intensity (%) |
|---|---|---|
| 4.68 ± 0.20 | d space (A) | 37 |
| 5.39 ± 0.20 | 18.862 ± 0.841 | 64 |
| 6.39 ± 0.20 | 16.406 ± 0.632 | 25 |
| 7.84 ± 0.20 | 13.834 ± 0.447 | 51 |
| 12.79 ± 0.20 | 11.272 ± 0.295 | 22 |
| 14.03 ± 0.20 | 6.922 ± 0.110 | 20 |
| 15.26 ± 0.20 | 6.314 ± 0.091 | 36 |
| 15.73 ± 0.20 | 5.805 ± 0.077 | 27 |
| 15.96 ± 0.20 | 5.634 ± 0.072 | 52 |
| 16.13 ± 0.20 | 5.551 ± 0.070 | 50 |
| 16.93 ± 0.20 | 5.494 ± 0.069 | 39 |
| 17.65 ± 0.20 | 5.236 ± 0.062 | 38 |
| 18.04 ± 0.20 | 5.024 ± 0.057 | 25 |
| 19.72 ± 0.20 | 4.918 ± 0.055 | 83 |
| 20.01 ± 0.20 | 4.501 ± 0.046 | 58 |
| 20.56 ± 0.20 | 4.438 ± 0.044 | 74 |
| 21.00 ± 0.20 | 4.320 ± 0.042 | 100 |
| 21.21 ± 0.20 | 4.231 ± 0.040 | 47 |

Figure 4:
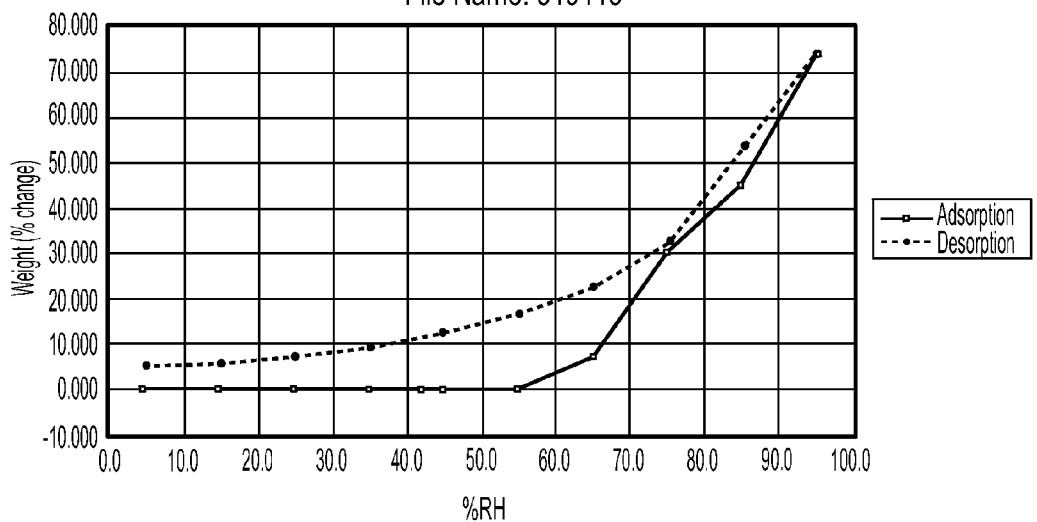
FIG. 4 presents an exemplary DVS graph showing the change in weight (in %) of BL-2010 MSA salt (Lot 01BIL02-07-34) as a function of relative humidity (RH)

DVS:

All lots showed less than 1% weight loss upon equilibration to 5% RH (see, Table 9). During the adsorption phase, data for these lots showed approximately 0.3% to 1.6% weight gain from 5-55% RH and then at least 69.9% weight gain from 55% to 95% RH. The samples did not reach equilibration from 55% to 95% RH. Also, the samples deliquesced during the adsorption phase. The samples exhibited significant hysteresis during the desorption phase, as all weight gained during the adsorption phase was not lost (about 5%). This may be due to the formation of a glass or oily material after deliquescence. A representative DVS graph is presented in FIG. 4.

TABLE 9

| | Moisture Balance Results | | | |
|---|---|---|---|---|
| Lot No. | Weight loss at 5% RH | Weight gain from 5-55% RH | Weight gain from 55-95% RH | Weight loss from 95-5% RH |
| 06-01915-3 | 0.6 | 0.6 | 71.6 | 66.9 |
| 01BIL02-01-22 | 0.1 | 0.4 | 71.6 | 67.0 |
| 01BIL02-02-22 | 0.1 | 0.4 | 69.8 | 64.8 |
| 01BIL02-03-22 | 0.1 | 0.4 | 72.7 | 67.6 |
| 01BIL02-04-22 | 0.1 | 0.4 | 70.5 | 66.0 |
| 01BIL02-05-26 | 0.3 | 0.4 | 68.9 | 64.8 |

Light Microscopy Evaluations:

Based on general light microscopy observations, material for lots 06-01915-3, 01BIL02-01-22, 01BIL02-02-22, 01BIL02-03-22, 01BIL02-04-22, 01BIL02-05-26 consisted of needles and spherulite fragments exhibiting birefringence with extinction. Material of lot 01BIL02-05-26 displayed more agglomeration than lots 06-01915-3, 01BIL02-01-22, 01BIL02-02-22, 01BIL02-03-22, and 01BIL02-04-22.

Figure 5A:
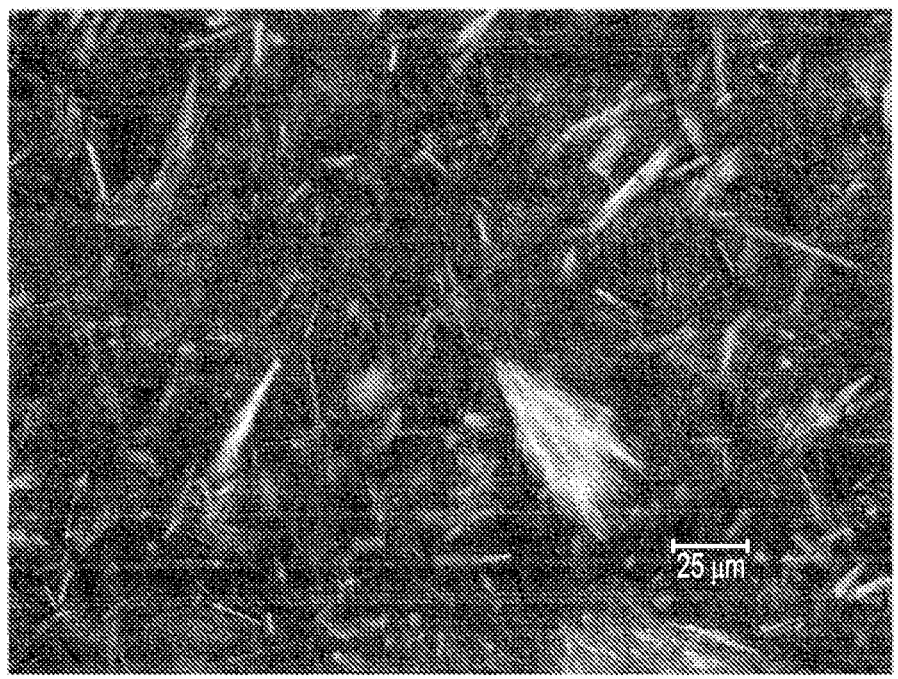
FIGS. 5A-B present images obtained by light microscopy of exemplary lots of crystalline Form B of BL-1020 MSA salt (Lot 01BIL02-04-22 in FIG. 5A and Lot 01BIL02-05-26 in FIG. 5B.

Representative photomicrographs are presented in FIGS. 5A (for lot 01BIL02-04-22) and 5B (for lot 01BIL02-05-26).

Figure 5B:
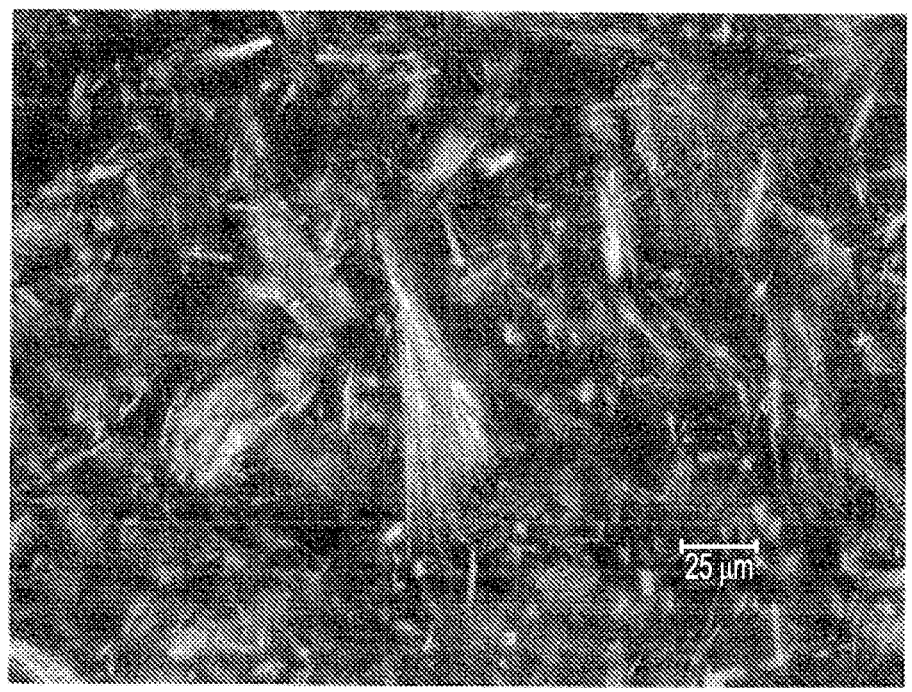

BET Surface Area:

Surface area results for lots 06-01915-3, 01BIL02-01-22, 01BIL02-02-22, 01BIL02-03-22 and 01BIL02-04-22 ranged from 4.57 to 4.93 $m^2/g$, and are summarized in Table 8 below. Results for lot 01BIL02-05-26 were lower, 2.67 $m^2/g$, presumably due to increased agglomeration (as observed in light microscopy; see, FIG. 5B).

TABLE 10

| Lot No. | Results ($m^2/g$) |
|---|---|
| 06-01915-3 | 4.84 |
| 01BIL02-01-22 | 4.77 |
| 01BIL02-02-22 | 4.55 |
| 01BIL02-03-22 | 4.93 |
| 01BIL02-04-22 | 4.57 |

Bulk and Tapped Densities:

The bulk and tapped density results for lots 06-01915-3, 01BIL02-01-22, 01BIL02-02-22, 01BIL02-03-22 and 01BIL02-04-22 are presented in Table 11 below, and ranged from 0.13 to 0.18 g/ml (bulk) and from 0.22 to 0.26 g/ml (tapped). Results for lots 01BIL02-05-26, 01BIL02-06-26 and 01BIL02-07-34 were higher and ranged 0.22 to 0.28 g/ml (bulk) and from 0.32 to 0.37 g/ml (tapped). The higher density for these lots is likely due to increased agglomeration/different particle shape noted in the light micrographs.

TABLE 11

| | Results (g/ml) | |
|---|---|---|
| Lot No. | Bulk density | Tapped density |
| 06-01915-3 | 0.18 | 0.24 |
| 01BIL02-01-22 | 0.16 | 0.25 |
| 01BIL02-02-22 | 0.16 | 0.24 |
| 01BIL02-03-22 | 0.18 | 0.26 |
| 01BIL02-04-22 | 0.13 | 0.22 |

Particle Size Sample Analysis:

The refractive index of BL-1020 MSA salt was measured microscopically using the Becke line method, and was determined to be 1.56 for the purpose of particle size analysis.

The measurement of particle size of all lots was performed using the same method conditions (in 0.1% SPAN 85 in hexane as a dispersing medium, sonication for 10 seconds, a pump speed of 1000 rpm and a recirculation time of 90 seconds). The results of the particle size distribution analysis in tuns of d10, d50 and d90 values are summarized in Table 12 below.

The data for lots 06-01915-3, 01BIL02-01-22, 01BIL02-02-22, 01BIL02-03-22, 01BIL02-04-22 showed predominantly unimodal distributions with a tail of fines below 1 μm, and particle sizes up to approximately 100 μm. However, data for lot 06-01915-3 showed a tendency towards higher particle sizes (d10, d50, and d90) than lots 01BIL02-01-22, 01BIL02-02-22, 01BIL02-03-22, 01BIL02-04-22.

Data for lot 01BIL02-05-26 were polydispersed, with an overall particle size range of 0.4 μm to greater than 1000 μm, in comparison to the other lots. This suggests that the agglomerates are harder (fused) and are not breaking.

TABLE 12

| Lot No. | d10 | d50 | d90 |
|---|---|---|---|
| 06-01915-3 | 3.8 | 9.3 | 41.8 |
| 01BIL02-01-22 | 2.1 | 5.8 | 18.3 |
| 01BIL02-02-22 | 2.1 | 6.1 | 22.5 |
| 01BIL02-03-22 | 2.1 | 6.2 | 19.7 |
| 01BIL02-04-22 | 2.3 | 6.8 | 21.8 |

Additional characterizing data for the tested BL1020 MSA salts are presented in U.S. Provisional Patent Application No. 61/307,481, filed Feb. 24, 2001, which is incorporated by reference as if fully set forth herein.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A crystalline form of perphenazine 4-aminobutyrate trimesylate, having at least one of:
    (a) an X-Ray Powder Diffraction (XRPD) pattern exhibiting at least five of the peaks selected from the group consisting of 2Θ values (in units of degrees) of about 4.7, 5.4, 6.4, 7.8, 12.8, 14.0, 15.3, 15.7, 16.0, 16.1, 16.9, 17.7, 18.0, 19.7, 20.0, 20.6, 21.0, and 21.2; and
    (b) a Differential Scanning Calorimetry (DCS) exhibiting an endothermic peak at between about 209° C. to about 214° C.

2. The crystalline form of perphenazine 4-aminobutyrate trimesylate of claim 1, having an X-Ray Powder Diffraction (XRPD) pattern exhibiting at least six of the peaks selected from the group consisting of 2Θ values (in units of degrees) of about 4.7, 5.4, 6.4, 7.8, 12.8, 14.0, 15.3, 15.7, 16.0, 16.1, 16.9, 17.7, 18.0, 19.7, 20.0, 20.6, 21.0, and 21.2.

3. The crystalline form of perphenazine 4-aminobutyrate trimesylate of claim 1, having an X-Ray Powder Diffraction (XRPD) pattern exhibiting at least seven of the peaks selected from the group consisting of 2Θ values (in units of degrees) of about 4.7, 5.4, 6.4, 7.8, 12.8, 14.0, 15.3, 15.7, 16.0, 16.1, 16.9, 17.7, 18.0, 19.7, 20.0, 20.6, 21.0, and 21.2.

4. The crystalline form of perphenazine 4-aminobutyrate trimesylate of claim 1, having an X-Ray Powder Diffraction (XRPD) pattern exhibiting the peaks consisting of 2Θ values (in units of degrees) of about 4.7, 5.4, 6.4, 7.8, 12.8, 14.0, 15.3, 15.7, 16.0, 16.1, 16.9, 17.7, 18.0, 19.7, 20.0, 20.6, 21.0, and 21.2.

5. A crystalline form of perphenazine 4-aminobutyrate trimesylate, having an X-Ray Powder Diffraction (XRPD) pattern exhibiting at least five of the peaks selected from the group consisting of 2Θ values (in units of degrees) of about 4.7, 5.4, 6.4, 7.8, 12.8, 14.0, 15.3, 15.7, 16.0, 16.1, 16.9, 17.7, 18.0, 19.7, 20.0, 20.6, 21.0, and 21.2.

6. A crystalline form of perphenazine 4-aminobutyrate trimesylate, having an X-Ray Powder Diffraction (XRPD) pattern exhibiting at least six of the peaks selected from the group consisting of 2Θ values (in units of degrees) of about 4.7, 5.4, 6.4, 7.8, 12.8, 14.0, 15.3, 15.7, 16.0, 16.1, 16.9, 17.7, 18.0, 19.7, 20.0, 20.6, 21.0, and 21.2.

7. A crystalline form of perphenazine 4-aminobutyrate trimesylate, having an X-Ray Powder Diffraction (XRPD) pattern exhibiting at least seven of the peaks selected from the group consisting of 2Θ values (in units of degrees) of about 4.7, 5.4, 6.4, 7.8, 12.8, 14.0, 15.3, 15.7, 16.0, 16.1, 16.9, 17.7, 18.0, 19.7, 20.0, 20.6, 21.0, and 21.2.

8. The crystalline form of perphenazine 4-aminobutyrate trimesylate of claim 5, having an X-Ray Powder Diffraction (XRPD) pattern exhibiting peaks having 2Θ values (in units of degrees) of about 4.7, 5.4, 6.4, 7.8, 12.8, 14.0, 15.3, 15.7, 16.0, 16.1, 16.9, 17.7, 18.0, 19.7, 20.0, 20.6, 21.0, and 21.2.

9. A crystalline form of perphenazine 4-aminobutyrate trimesylate having a Differential Scanning Calorimetry (DSC) exhibiting an endothermic peak at between about 209° C. to about 214° C.

10. The crystalline form of perphenazine 4-aminobutyrate trimesylate of claim 1, having a purity greater than 99%, as determined by HPLC area percentage measurements.

11. The crystalline form of perphenazine 4-aminobutyrate trimesylate of claim 1, having an average particle size smaller than 100 microns.

12. The crystalline form of perphenazine 4-aminobutyrate trimesylate of claim 11, wherein said average particle size is smaller than 10 microns.

13. The crystalline form of perphenazine 4-aminobutyrate trimesylate of claim 1, being shaped as needles.

14. The crystalline form of perphenazine 4-aminobutyrate trimesylate of claim 1, having a surface area higher than 2.5 $m^2/g$.

15. The crystalline form of perphenazine 4-aminobutyrate trimesylate of claim 14, having a surface area that ranges from 4.5 $m^2/g$ to 5 $m^2/g$.

16. The crystalline form of perphenazine 4-aminobutyrate trimesylate of claim 1, prepared by reacting N-protected perphenazine 4-aminobutyrate and methanesulfonic acid, in the presence of a mixture of acetonitrile and butyl acetate as a solvent.

17. A process for preparing the crystalline form of claim 1, the process comprising reacting an N-protected perphenazine 4-aminobutyrate and methanesulfonic acid, in the presence of a mixture of acetonitrile and butyl acetate, thereby producing the crystalline form of perphenazine 4-aminobutyrate trimesylate.

18. The process of claim 17, wherein said N-protected group is N protected with t-butoxycarbonyl.

19. The process of claim 17, wherein said reacting comprises:
   (i) dissolving said N-protected perphenazine 4-aminobutyrate in said mixture of acetonitrile and butyl acetate; and
   (ii) adding a solution of methanesulfonic acid in acetonitrile to the solution of said N-protected perphenazine 4-aminobutyrate in said mixture of acetonitrile and butyl acetate.

20. The process of claim 19, wherein the solution of said N-protected perphenazine 4-aminobutyrate in said mixture of acetonitrile and butyl acetate is heated to about 40° C.

21. The process of claim 17, further comprising isolating the crystalline form of perphenazine 4-aminobutyrate trimesylate from the reaction mixture.

22. The process of claim 17, further comprising purifying the perphenazine 4-aminobutyrate trimesylate salt.

23. A pharmaceutical composition comprising the crystalline form of perphenazine 4-aminobutyrate trimesylate of claim 1 and at least one pharmaceutically acceptable carrier.

24. The pharmaceutical composition of claim 23, packaged in a packaging material and identified in print, in or on said packaging material, for use in the treatment of schizophrenia.

25. A method of treating schizophrenia, the method comprising administering to a subject in need thereof a therapeutically effective amount of the crystalline form of perphenazine 4-aminobutyrate trimesylate of claim 1, thereby treating schizophrenia.

\* \* \* \* \*